United States Patent [19]

Marshall, III

[11] Patent Number: 4,946,793
[45] Date of Patent: Aug. 7, 1990

[54] IMPEDANCE MATCHING FOR INSTRUMENTATION WHICH ELECTRICALLY ALTERS VESICLE MEMBRANES

[75] Inventor: John Marshall, III, Boulder, Colo.

[73] Assignee: Electropore, Inc., Boulder, Colo.

[21] Appl. No.: 283,215

[22] Filed: Dec. 12, 1988

Related U.S. Application Data

[63] Continuation-in-part of Ser. No. 47,208, May 8, 1987, which is a continuation-in-part of Ser. No. 861,534, May 9, 1986, abandoned.

[51] Int. Cl.$^5$ .................... C12N 13/00; C12N 15/00
[52] U.S. Cl. .................................. 435/291; 435/173; 435/289; 435/287; 935/52; 935/89; 935/93
[58] Field of Search ............... 435/173, 287, 289, 291; 935/52, 89, 93; 204/299 R, 183.1, 180.1

[56] References Cited

U.S. PATENT DOCUMENTS

| | | | |
|---|---|---|---|
| 4,476,004 | 10/1984 | Pohl | 204/299 R |
| 4,622,302 | 11/1986 | Sowers | 435/172.2 |
| 4,663,292 | 5/1987 | Wong et al. | 435/287 |
| 4,750,100 | 6/1988 | Ragsdale | 363/86 |

OTHER PUBLICATIONS

Tsong, "Electric Modification of Membrane Permeability for Drug Loading into Living Cells", Methods in Enzymology, vol. 149 (1987), 248-259.

*Primary Examiner*—John F. Niebling
*Assistant Examiner*—John S. Starsiak, Jr.
*Attorney, Agent, or Firm*—Dorr, Carson, Sloan & Peterson

[57] ABSTRACT

The instrument of the present invention is designed to electrically alter membranes of vesicles in a suspension in order to perform vesicular alteration and electrostructuring of the membranes. The instrument includes a supply for delivering voltage to a pulse forming network. The output of the pulse forming network is selectively switched to deliver one or a plurality of output pulses across a chamber holding the suspension. Disposed in the chamber are a pair of electrodes which define a geometry for applying either a non-uniform field across the suspension or defining a uniform field across the suspension. The present invention is not limited to the type of field uniformity. Connected in parallel across the electrodes is a device for matching the impedance of the chamber containing the suspension of vesicles. This device is in parallel combination with the chamber and when properly adjusted, matches the impedance of the chamber to the pulse forming network.

The device for matching the impedance can be manually or automatically controlled, such as through a computer, to selectively switch in a one or a plurality of parallel resistances until the impedance of the chamber matches the impedance of the pulse forming network. To properly determine the impedance of the chamber, a separate circuit delivers one or a plurality of low voltage pulses across the chamber, measures the resulting current flow and based upon that measurement selectively interconnects the parallel resistances until the chamber, in parallel combination with the resistances, equals the impedance of the pulse forming network.

In this fashion, the treatment pulses being applied to the chamber containing the suspensions, despite possible wide variations of impedances for the chamber and the suspensions, insures precise reproducibility of the treatment pulses.

15 Claims, 13 Drawing Sheets

OUTPUT WAVEFORM

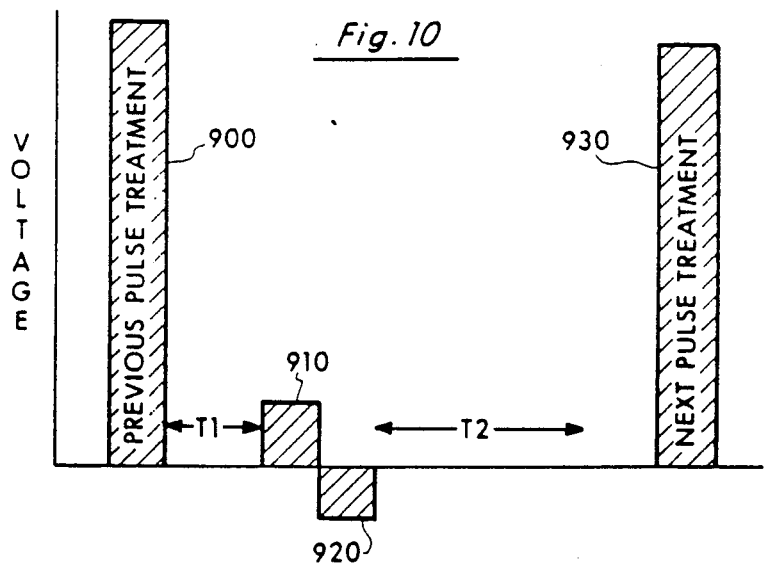
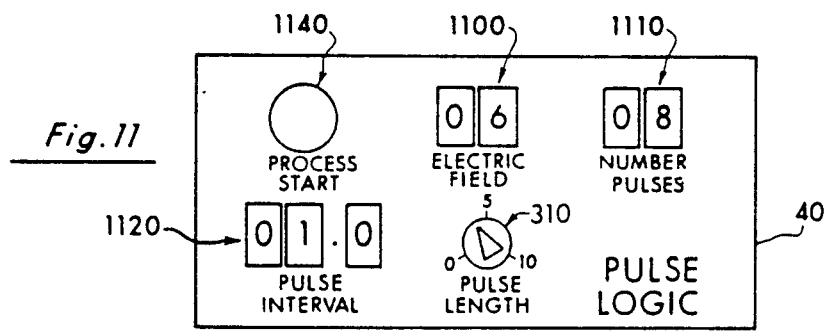
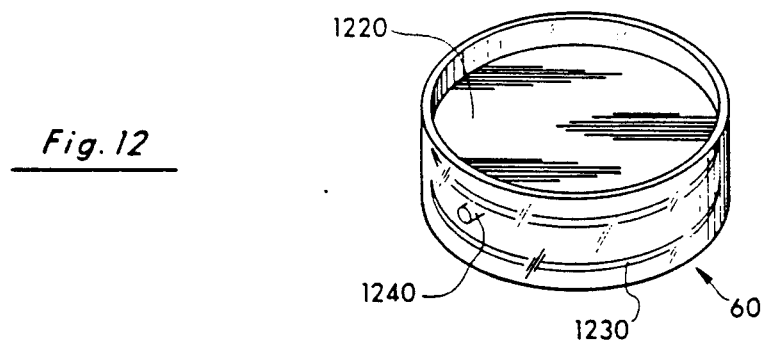

IMPEDANCE MATCHING FOR INSTRUMENTATION WHICH ELECTRICALLY ALTERS VESICLE MEMBRANES

BACKGROUND OF THE INVENTION

1. Related Applications

This is a continuation-in-part of application Serial No. 07/047,208, filed May 8, 1987 entitled "High Speed, High Power Apparatus for Vesicle Prealignment, Poration, Loading and Fusion in Uniform Electric Fields and Method Therefor" which is a continuation-in-part of Ser. No. 06/861,534, filed May 9, 1986, now abandoned. This is also related to "The Alteration of Vesicle Membranes Using Multiple Pulses of Controlled Time Intervals", Ser. No. 07/283,222, filed concurrently herewith.

2. Field of the Invention

The present invention is related to an apparatus and process for applying high intensity electric field pulse treatments to vesicles in liquid suspension. Vesicle is herein defined as a body which resembles a bladder especially in constituting a small thin-walled cavity such as (a) a plant or animal structure (e.g., a cyst, vacuole, or cell) or (b) a non-biological structure (e.g., as a liposome or microsphere) having the general form of a membranous cavity such as a thin sac and especially when filled with fluid. Cells are generally defined as microscopic masses of protoplasm bounded externally by a semi-permeable membrane.

More particularly, this invention sets forth an apparatus and process for matching the impedance of the chamber containing the vesicles in suspension before applying high intensity electrical pulses to perform vesicular alterations.

3. Statement of the Problem

It is well known that vesicular structures can be altered through the application of electric fields (i.e., electromanipulation). For example, electroporation is a type of electromanipulation of a biological membrane such that a style of permeability is induced in the membrane which acts like small holes or "pores." This process establishes a semi-stable membrane state such that molecules and macromolecules may cross the otherwise impermeable membrane barrier. This semi-stable state may be reversed and repaired upon warming the membrane in question. If stored at low temperatures, however, the semi-stable membrane state can exist for hours or days. Electroporation has been successfully utilized to create semi-stable membrane states in a number of different cell types such as cultured cell lines, mammalian primary cell cultures, mammalian and embryonic stem cells, isolated intracellular vesicles, dicot and monocot plant protoplasts, protists and bacteria. Electroporation has been used to introduce DNA molecules, to load cells with dyes and other molecules, and to extract molecules from cells without requiring cell lysis. See "Introduction and Expression of DNA Molecules in Eukaryotic Cells by Electroporation", Volume 6, No. 7, BIOTECHNIQUES (1988), Page 650. The use of electric fields to transfer biological macromolecules such as genetic material (DNA), RNA, and protein into cells is well known. See Wong, U.S. Pat. No. 4,663,292, "High-Voltage Biological Macromolecule Transfer and Cell Fusion." Another form of electromanipulation is fusion. Fusion is defined as the merger or coalescence of at least two vesicles to form a single vesicular entity. For example, see Sowers, U.S. Pat. No. 4,622,302, "Process for Inducing Membrane Fusion Under an Electric Field."

Various instruments have been devised to electrically manipulate vesicles in suspension. These instruments essentially comprise a high voltage source which delivers electric pulses and a chamber which holds the vesicle suspension and receives the electric pulse. An example of high voltage source instrumentation is described by Ragsdale "Transfection High Voltage Controller", U.S. Pat. No. 4,750,100 issued June 7, 1988. Ragsdale teaches that multiple SCRs may be connected in series to support voltages over 3,000 volts and currents in excess of 125 amperes. Owing to the use of capacitor discharge, the output of the Ragsdale instrument is a single high-voltage, high-energy, exponentially decaying pulse or a truncated pulse which approximates a rectangular pulse. Ragsdale describes an upper load limitation of 1000 ohms and his instrument does not trigger above 1000 ohms. No impedance matching circuitry is discussed in Ragsdale.

The electric field treatment processes necessary to accomplish such vesicular membrane alteration fall into two distinctly different categories. The first category of processes utilizes electrodes which generate non-uniform electric fields across a chamber containing vesicles in a suspension. The non-uniform electric fields are created by the geometric configuration of the electrodes. Hence, vesicles at different physical locations within the chamber are subjected to different (often radically different) impressed electric fields which according to the proponents are required for the practice of the art. Examples of such non-uniform field approaches are the Wong and Sowers patents supra.

Wong provides biological macromolecule transfer and cell fusion with a system providing uncontrollable high-voltage discharge output pulses from a low input voltage. Wong suspends a conical electrode above a chamber holding a suspension (from 1 to 10 milliliters) containing cells (e.g., 10,000,000 cells). Application of power to the appropriate circuitry of the instrument then elevates the voltage through autotransformer action, thereby causing sparks to form between the electrode and the chamber, thus energizing the solution. This non-contacting electric field approach creates a non-uniform field as applied across the suspension. Wong utilizes a number of cycles (CY) of pulse bursts (B) wherein each burst has a number of rectangular input pulses (NP) of a given pulse duration (P). Wong converts a low voltage such as 24 volts into a high voltage having an amplitude (A) up to 10 KV using a step-up transformer. The range of the bursts (B) may be from 0.05 seconds to 12.8 seconds, the number of cycles (CY) may vary to infinity, a pulse duration (P) fixed at 62.5 microseconds, and the number of pulses (NP) may be from one to 2048. Duration (P) as used by Wong includes the actual pulse duration plus the interval of time before the next pulse. In Wong's two examples, a 7.5 KV to 10 KV amplitude pulse was utilized. The number of pulses varied from 32 to 64, the burst time varied from 0.05 seconds to 0.2 seconds and the number of cycles varied from 10 to 20. Although the low voltage input pulse form is rectangular, the final output pulse form is not due to inductive step-up transformation, capacitive chamber reactance, and the absence of impedance matching of the chamber to the generator.

In Sowers, two wire electrodes are anchored to a frame made from a standard microscope slide to apply a non-uniform electric field across a fusion chamber formed there between. Sowers uses 2-30 pulses of direct current (each pulse having a rise time not exceeding 10 microseconds, with an exponentially decaying fall time) at a rate of 2 to 5 pulses per second which alter cell membranes to a fusogenic state. The electrical field strength of these pulses varies between 5000-10000 volts/cm. The exponential decay half time of each pulse ranges from 0.2 milliseconds to 1.2 milliseconds. Sowers utilizes a conventional variable voltage (0-1000 V) electrophoresis-type power supply which limits the process to essentially high impedance chambers (i.e. low volume or high resistance) because of the power limitations of the supplies. Sowers does not disclose the use of impedance matching circuitry.

The second category of processes utilizes electrodes which generate uniform electric fields across a chamber used to hold vesicles in a suspension. Hence, any point in the chamber is subjected to the same impressed uniform, homogeneous field generated by the parallel plate electrodes. An example of such a uniform approach is Tsong, "Electric Modification of Membrane Permeability for Drug Loading Into Living Cells", Methods in Enzymology, Vol. 149 (1987), pgs. 248-259 wherein a treatment chamber of approximately 1 ml of two parallel opposing hollow stainless steel electrodes are separated by 2 mm. Tsong uses a Cober 605P high-voltage generator (2.2 KV with a maximum power of 24 KW) with a Cober Model P27 Pulse Generator to impress a single pulse across the chamber with widths ranging up to 100 microseconds at a voltage up to 4 Kv/cm. Tsong's preferred treatment applies a field intensity of 2.2 Kv/cm with a single 20 microsecond pulse for small molecules and ions. For large molecules, Tsong's preferred treatment is a single 3.7 Kv/cm field intensity 20 microsecond pulse. The Cober generator is limited to solutions which exhibit impedances in a range always greater than 200 ohms. There is no circuit in Cober which matches the impedance of the chamber to the generator.

The uniform field treatment for electromanipulation of vesicles represents an approach to electric field treatment of materials and alteration of vesicular membranes which is quite different from the non-uniform field treatment approaches.

A need exists for a method and apparatus which improves upon the control of electrically induced vesicle alteration through matching the impedance of the chamber to the generator before application of a treatment pulse to the chamber. This need exists for both the non-uniform treatment pulse applications or the uniform treatment pulse applications. When the apparatus applying the non-uniform field or the apparatus applying the uniform field is properly matched to the chamber containing the suspensions, the waveform is accurately applied thereby providing better control over the vesicular alteration process and producing higher reproducibility of electrically induced vesicular alterations. The impedance across the chamber can vary significantly based upon the conductivity of the suspension and the design of the chamber. None of the above prior references, whether for the delivery of non-uniform field or of uniform field pulses utilize impedance matching circuits before the delivery of the electric field treatment pulse to the chamber.

4. Solution to the Problem

The present invention provides a solution to the above problem with an apparatus and process for matching the impedance of the chamber to the pulse generator before the application of the treatment pulses.

The present invention with its improved impedance matching component furthermore enables more repeatable electric field treatments to suspensions of vesicles over a wide range of conductivity. The ability to set and control important parameters such as pulse length, pulse form, pulse decay time, pulse rise time, and pulse fall time, that when applied to the chamber remain independent and unaffected by the characteristics of the solution contained therein, is critical to obtain such repeatability.

The present invention, therefore, provides an improved method and apparatus for electromanipulation of vesicles which can be applied to a variety of vesicles such as biological cells suspended in solution.

The present invention, in the preferred embodiment, sets forth an impedance matching technique for use in applying uniform electric field across a chamber. However, the teachings of the present invention apply to apparatuses which apply non-uniform electric fields across chambers.

The present invention furthermore provides for a means to match load impedance to pulse generator impedance wherein the driver can be a pulse forming network such that electrical field effects on vesicles in suspension will be substantially the same from treatment to treatment and wherein the parameters of the field treatment once selected will not be affected by the impedance of the treatment chamber.

The present invention additionally provides a means for impedance matching during continuous processing of large volumes of material.

The instrument of the present invention includes a high voltage power supply, a pulse forming network for applying a series of treatment pulses across the chamber containing the suspended vesicles, a rapid rise time switch for selectively delivering each of the pulses from the pulse forming network across electrodes contained in the chamber, and means for matching the impedance of the chamber to the impedance of the pulse forming network.

The impedance matching apparatus of the present invention utilizes a plurality of low voltage pulses which are first applied across the chamber to generate an impedance signal which is compared to a reference value. In the event the impedance signal varies from the reference value, a parallel shunt resistance across the chamber is selectively changed to match the impedance.

SUMMARY OF THE INVENTION

The instrument of the present invention is designed to electrically alter membranes of vesicles in a suspension in order to perform vesicular alteration and electrostructuring of the membranes. The instrument includes a supply for delivering voltage to a pulse forming network. The output of the pulse forming network is selectively switched to deliver one or a plurality of output pulses across a chamber holding the suspension. Two of the chamber components are a pair of electrodes which define a geometry for applying either a non-uniform field across the suspension or defining a uniform field across the suspension. The present invention is not limited to the type of field uniformity. Connected in parallel across the electrodes is a device for matching the impedance of the chamber containing the suspension of vesicles. This device is in parallel combination with the chamber and when properly adjusted, matches the impedance of the chamber to the pulse forming network.

The device for matching the impedance can be manually or automatically controlled, such as through a computer, to selectively switch in one or a plurality of parallel resistances until the impedance of the chamber matches the impedance of the pulse forming network. To properly determine the impedance of the chamber, a separate circuit delivers one or a plurality of low voltage pulses across the chamber, measures the resulting current flow and based upon that measurement selectively interconnects the parallel resistances until the chamber, in parallel combination with the resistances, equals the impedance of the pulse forming network.

In this fashion, control of the treatment pulses being applied to the chamber containing the suspensions, despite possible wide variations of impedances for the chamber and the suspensions, insures precise reproducibility of the treatment pulses.

BRIEF DESCRIPTION OF THE DRAWING

FIG. 10 sets forth a graphical illustration of impedance matching after the application of each treatment pulse;

FIG. 11 is a diagram showing the operator controls in the pulse logic circuit 40 of the present invention;

FIGS. 12 and 13 set forth the structure of the chamber 60 of the present invention;

DETAILED DESCRIPTION

1. Electronics

Figure 1:
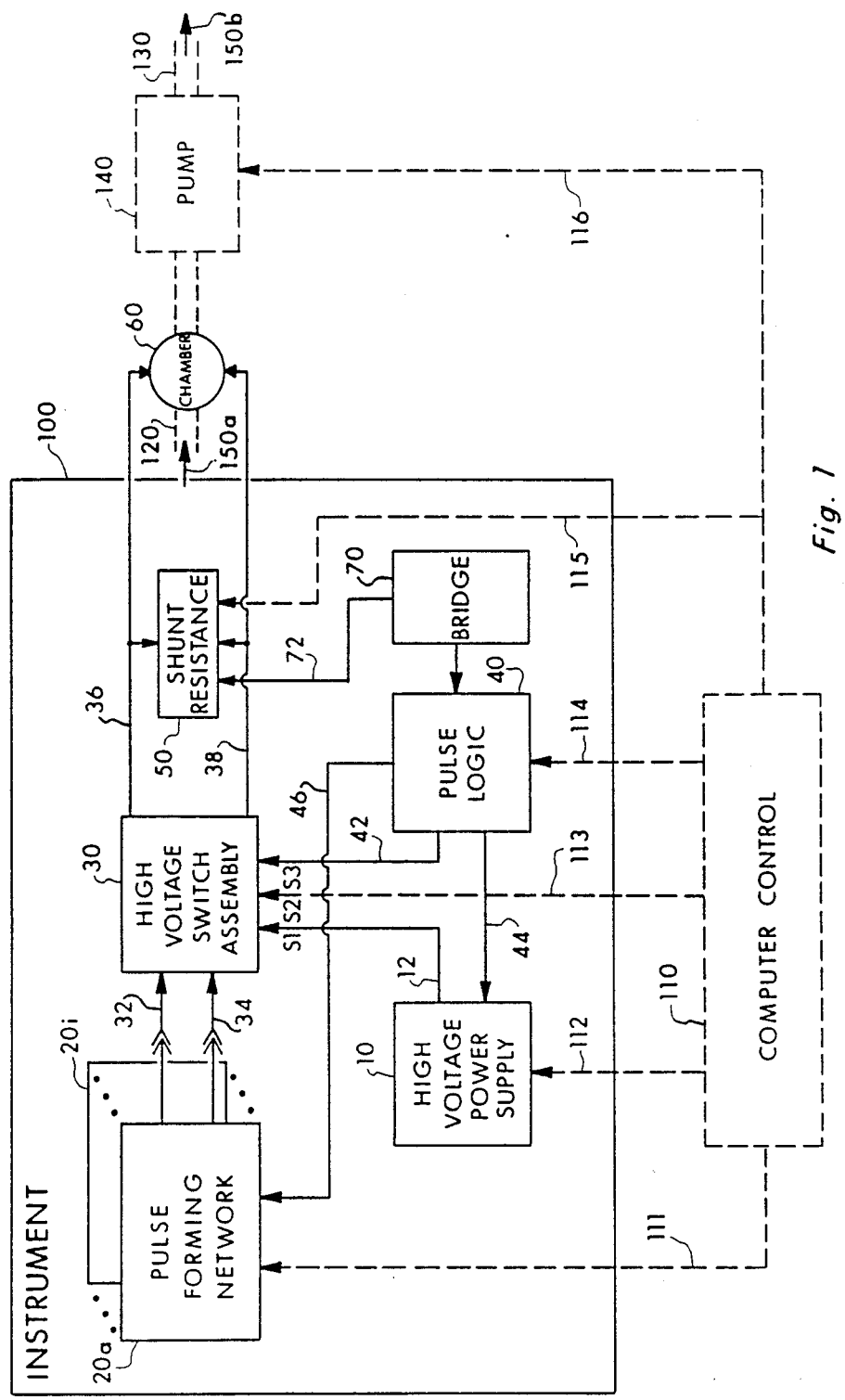
FIG. 1 sets forth the block diagram for the instrument of the present invention under optional computer control.

In FIG. 1, the instrument 100 of the present invention is set forth to include a high voltage power supply 10, one or a plurality of plug in pulse forming networks 20a–i (each of which can be selectively plugged into the instrument), a high voltage switch assembly 30, pulse logic 40, a shunt resistance 50, a bridge circuit 70 and a chamber 60 (which may be either flow-through or non-flow-through).

The instrument 100 may also be part of a system shown in dotted lines controlled by computer 110 interconnected with a flow-through chamber 60 having an inlet 120 and an outlet 130 interconnected with a device such as a pump 140 to control the flow of liquid suspension through the chamber 60 as shown by arrows 150a and 150b. The computer 110 could be a separate stand alone computer such as an IBM PC Series II or a microprocessor installed within the instrument 100. The computer controls the pulse forming network 20 over lines 111, the high voltage power supply 10 over lines 112, the high voltage switch assembly 30 over line 113, the pulse logic 40 over lines 114, the shunt resistance 50 over lines 115 and the pump 140 over lines 116.

It is to be expressly understood that the computer control 110 could also operate a non-flow-through chamber 60 by eliminating the lines 116, pump 140 and ports 120 and 130.

Each of the components of the instrument 10 is discussed in greater detail in the following.

a. High Voltage Power Supply 10

The high voltage power supply 10, in the preferred embodiment, can be of the type that is shown in the above identified related patent application. The power supply used in the Examples, infra, high voltage power is capable of delivering enough power to charge the pulse forming network 20 to maintain the desired pulse repetition rate. For the Examples infra, supply 10 is capable of delivering 100 milliamps of current up to 10 kilovolts, a power of 1000 watts, to maintain a pulse rate of twenty times per second. The high voltage power supply delivers its high voltage output over line 12 to the pulse forming network 20 through switch 30.

b. High Voltage Switch Assembly 30

The high voltage switch assembly 30 in FIG. 1 consists of high voltage, high current switches which can operate at thousands of volts and at hundreds of amperes with nanosecond rise times. High speed switch assembly 30 is interconnected to the pulse forming network 20 over lines 32 and 34 and is further interconnected to the parallel combination of the shunt resistance 50 and the chamber 60 over lines 36 and 38. The high voltage switch assembly 30 receives control signals over line 42 from the pulse logic 40.

Figure 2:
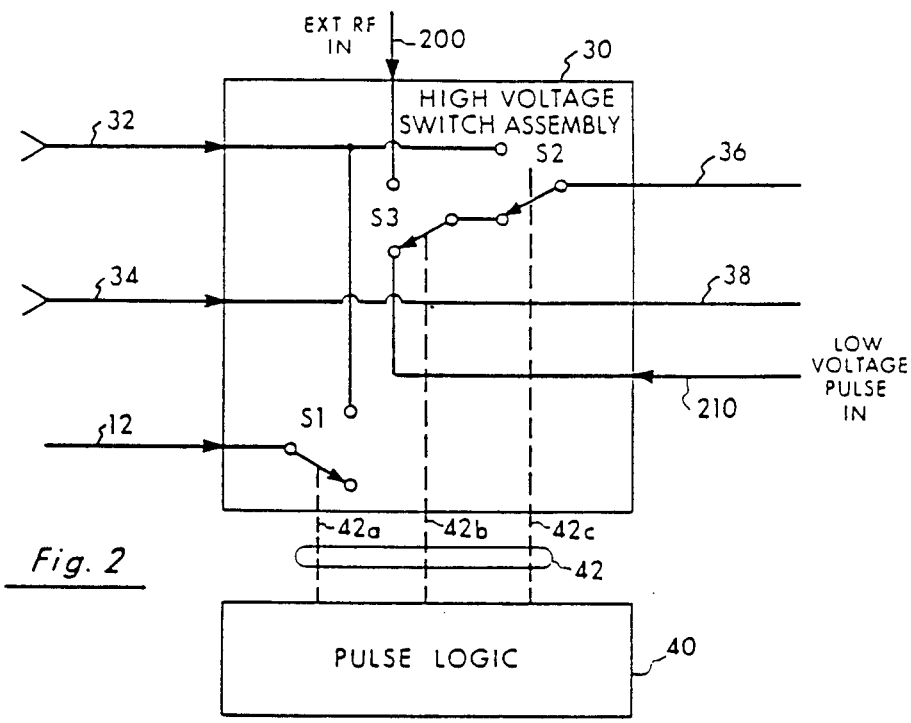
FIG. 2 is the schematic for the high voltage switch assembly 30 of the present invention.

In FIG. 2, the details of the high voltage switch assembly 30 is set forth to include three separate switches S1 to S3.

Switch S1, a high-voltage reed relay, type 500801501180 available from Aleph International Corp., 1026 Griswald Avenue, San Fernando, Calif. 91340 is activated by line 42a from the pulse logic 40 to close. When closed switch S1 connects line 12 from the supply 10 to line 32 in order to charge the pulse forming network 20. After charging is completed, switch S1 is then opened.

Switch S2 of FIG. 2, depending on requirements, could be a thyratron, spark gap, ignitron, trigatron or gas filled relay. These devices allow extremely fast power switching. Switch S2 is also capable of operating at speeds of one to hundreds of closures per second. For example, when the switch S2 is a gas-filled relay, such as the type used in defibrillator devices, switch S2 is capable of being closed at rates up to 20 Hz. A gas-filled relay, Model No. RGD-1 available from Jennings (Division of FL Industries), 970 McLaughlin Avenue, San Jose, Calif. 95122 was used in the Examples, infra. To permit closure operations on the order of 1000 closures per second, switch S2 is a thyratron or spark gap switch. When it is desired to pulse chamber 60, the pulse logic 40 over line 42c causes switch S2 to close, connecting line 36 to line 32 to deliver, at nanosecond rise times, the charge from the network 20 across the chamber 60.

Switch S3, for example a standard low-voltage, single pole, double throw mercury-wetted relay, is used to deliver externally generated electrical fields across the chamber. Mercury wetting of the contacts provides low resistance switching. For example, an RF (radio frequency) field may be delivered from line 200 to line 36 by closing switch S3 and opening switch S2. The RF field may be used for prealignment of the vesicles as a preliminary step for alteration. Also shunt pulses may be applied across the chamber by opening both switches S3 and S2 thereby connecting line 210 to line 36. As will be explained, shunt pulses are used to automatically match the impedance of the chamber 60 to the network 20.

c. Pulse Forming Network 20a–20i

Switch S2 of the high voltage switch assembly 30 provides high speed contact between a charge accumulator, such as the pulse forming network 20, and the parallel combination of the shunt resistance 50 and the chamber 60. The shunt resistance 50, in parallel with the resistance of the chamber 60, is designed to produce the same value of resistance to the switch 30 for each pulse delivered from the network. In this manner, the pulse forming network 20 will always be driving its characteristic impedance which in the preferred embodiment is 16.7 ohms. This insures that the pulse form and amplitude will be reproducibly delivered across the chamber 60 for each pulse repetition.

A pulse forming network is generally defined as a set of electrical circuits where more than one closed path exists. As applied to the alteration of vesicles, the use of interchangeable plug-in pulse forming networks in the instrument 100 of the present invention allows for the generation of virtually any pulse form with a desired amplitude.

Prior art references are limited to fixed pulse forms based upon their inherent design. The present invention provides a plurality of plug-in pulse forming networks which provide virtually any desired pulse form for altering vesicles. Essentially, a pulse forming network stores a set amount of electrical energy. The pulse forming network can also be connected to other series and parallel combinations of load (i.e., the chamber) to give a specific pulse form or impedance matching characteristics to the delivered uniform electric field impressed across the chamber 60.

Figure 3:
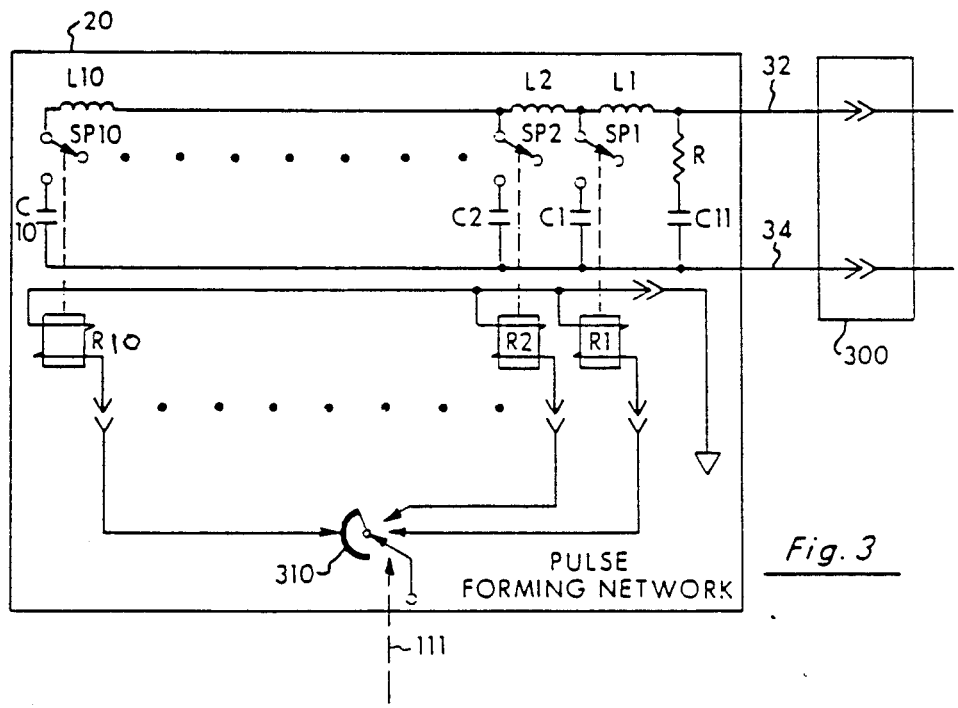
FIG. 3 is a schematic for one of the pulse forming networks 20 of the present invention.

In FIG. 3, the plug-in pulse forming network 20 contains ten cascaded L/C stages comprising ten inductors L1 through L10 and ten capacitors C1 through C10 plus the resistor R and capacitor C11. The L/C combination provides virtually rectangular output pulses on lines 32 and 34. Network 20 plugs into connector 300 which connects with switch assembly 30.

A switch is provided for each stage and, therefore, ten switches SP1 through SP10 are provided. For example, assume switches SP1 through SP5 of the pulse forming network 20 of FIG. 3 are closed. Each switch is controlled by a relay R1-R10 which in turn is activated by relay control 310 which may be manually operated by the user of the instrument 100 of the present invention or, through a suitable mechanical link, automatically by computer control 110 over linkage 111. The selective closure of switches SP1 through SP10 allows the selection of specific pulse length.

Figure 4:
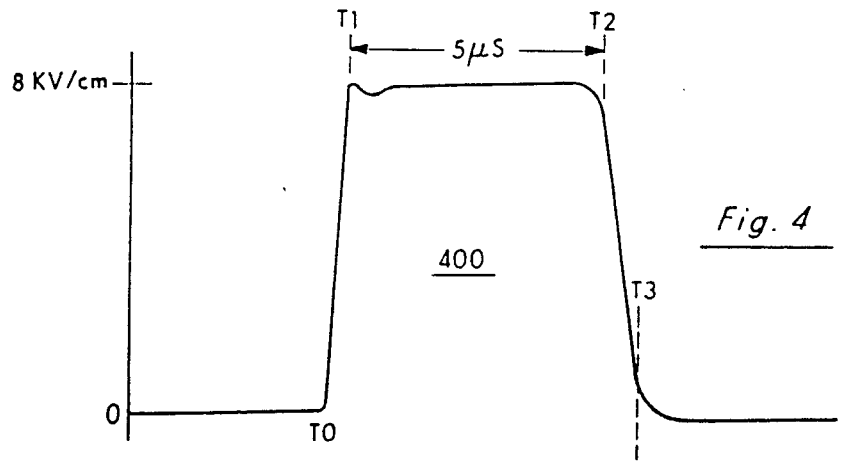
FIG. 4 is a graphical illustration of an output pulse form of the network of FIG. 3.

In reference to FIG. 4, at time, T0, the output of the pulse forming network 20 of FIG. 3 is virtually a rectangular 8 Kv/cm pulse 400. This pulse appears as it is applied across the parallel combination of the shunt resistance 50 and the chamber 60. The pulse of FIG. 4 has a fast rise time across the chamber, from T0 to T1, of less than 200 nanoseconds. The width of the pulse of FIG. 4 is five microseconds and a fall time from T3 to T4 of 700 nanoseconds (from 90% to 10% of the peak pulse voltage). The pulse of FIG. 4 is representative of the pulses used in the Examples discussed later.

The pulse forming network 20 of the present invention provides means to generate a multiplicity of pulse forms at the high voltages and high currents necessary to obtain the desired field strength across high conductivity vesicle suspensions in the chamber 60. For example, such high conductivity suspensions are typically 18 ohms at room temperature for isotonic saline solutions (56 millimhos) as measured across the 0.5 cm, 1 ml volume chambers 60 used in the Examples.

In summary, the pulse forming network 20 shown in FIG. 3 generates a rectangular output pulse shown in FIG. 4. The network combination of inductors L1 through L10 in combination with capacitors C1 through C10 and C11 and R generate the output pulse 400. Closing switches SP1 through SP10 increases the pulse duration. For example, closing SP1 and SP2 provides a pulse duration of two microseconds. Closing switches SP1 through SP10 provides a pulse duration of ten microseconds. It is to be expressly understood that L/C values can be modified in the network to provide different switch, SP, increments such as 2 microseconds, 5 microseconds, etc.

The addition of capacitor C11 and variable resistor R allows the user to decrease the rise time T0–T1 for pulse 400 of FIG. 4.

Figure 5:
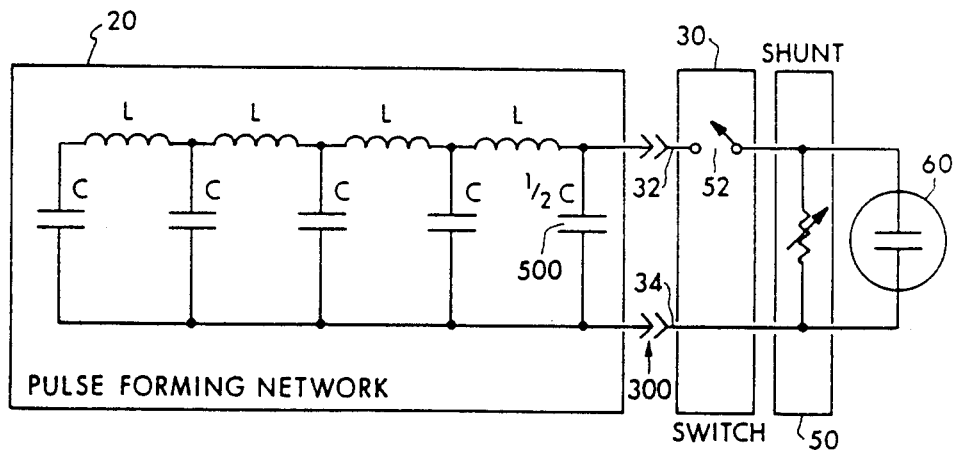
FIG. 5 is a schematic for a second pulse forming network 20 of the present invention.
Figure 6:
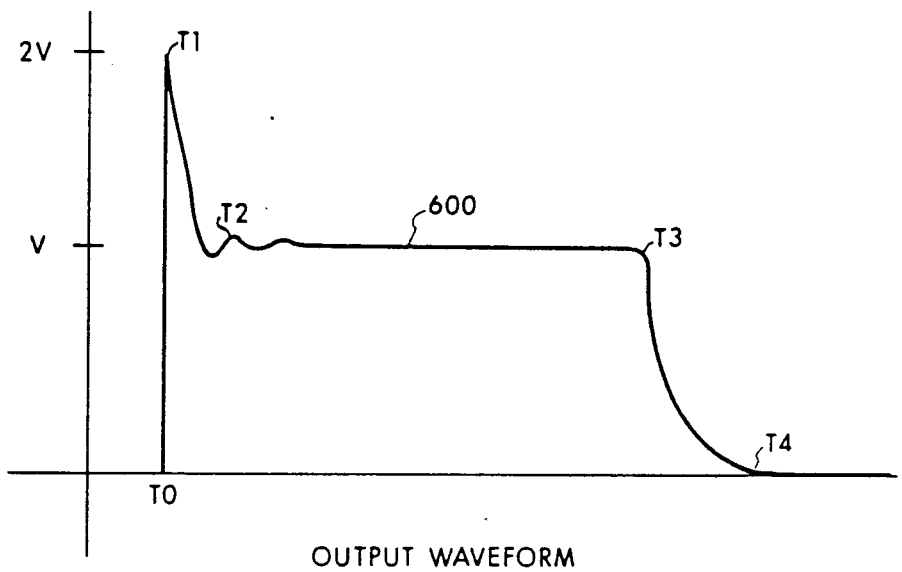
FIG. 6 is a graphical illustration of the composite output pulse form of the network of FIG. 5.

In FIGS. 5 and 6, a second embodiment of the plug-in pulse forming network 20 produces a more complex pulse form 600. This pulse form at time T0 undergoes a fast rise time (e.g., less than 200 nanoseconds) and then at time T1 decays to a sustaining half voltage level at time T2. This level is maintained until time T3 whereupon it exponentially decays away at time T4. The network shown in FIG. 5 is similar to that of FIG. 3 except for the use of a sustaining capacitor 500. The network of FIG. 5 is representative of the variety of pulse forms that can be generated by plugging different networks 20a–Ci into the present invention.

While the preferred embodiment of the pulse forming network discussed above has impedance of 16.7 ohms, the present invention is not so limited and such networks may be suitably designed in a range of impedances such as, for example, an impedance of 2 ohms.

As shown in FIGS. 1, 3 and 5, a plurality of pulse forming networks, are made as plug-in units in the apparatus of the present invention to permit the quick change from one style of pulse to another. Hence, a novel approach to the generation of a multiplicity of pulse forms into low impedance loads is set forth. Although pulse forming networks are disclosed, other suitable networks could be likewise used as plug-in units under the teachings of the present invention. The use of the pulse forming networks of the present invention finds application in instruments which apply either uniform or non-uniform electric field pulses to chambers.

d. Shunt Resistance 50 and Bridge Circuit 70

Figure 9:
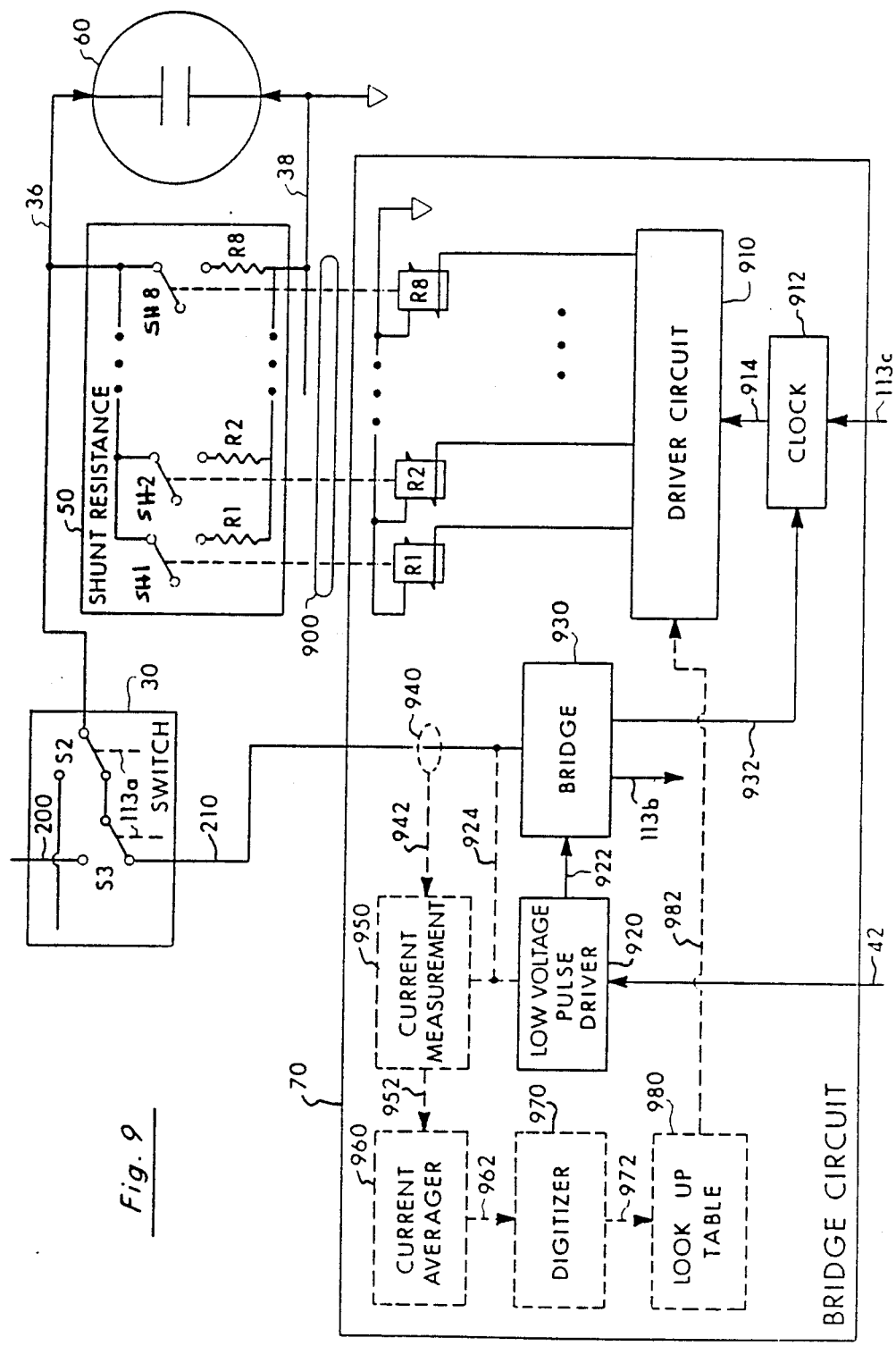
FIG. 9 is a block diagram of the shunt resistance and bridge circuit of the present invention used for impedance matching.

This action discusses the impedance matching capabilities of the present invention for use in the application of uniform electric fields as dictated by the geometry of chamber 60. These teachings can be applied for use in the application of non-uniform electric fields. In FIG. 9, the circuitry for the shunt resistance 50 is shown to include a plurality of parallel resistors R1 through R8 interconnected in parallel by means of a plurality of switches S1 through S8. The shunt resistance circuit 50 has for its purpose the matching of the impedance of the pulse forming network 20 across the chamber 60. Under the teachings of the present invention, the pulse forming network 20 will deliver precisely the same pulse form across the chamber each time it is discharged because of the constant impedance provided by the impedance matching.

The chamber 60 when filled with various biological solutions can exhibit a wide range of different impedances and, therefore, the shunt resistance circuit 50 of the present invention is designed such that the combined resistance of the chamber/shunt resistance combination of the pulse forming network 20 equals the constant impedance of FIGS. 1, 3, and 5.

Figure 7:
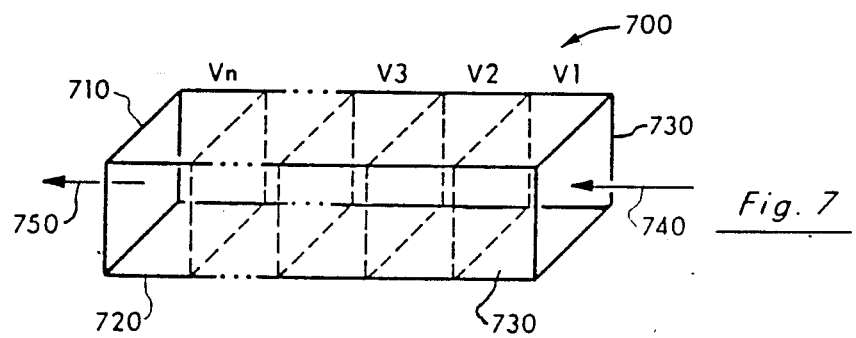
FIG. 7 is a diagram showing a rectangular uniform field pulsing chamber designed for flow-through multiple pulsing.

For example, in the embodiment shown in FIG. 7, chamber 60 can have any resistance from zero to infinity. If the resistance of chamber 60 is greater than or equal to the impedance of the pulse forming network 20 across lines 32 and 34 of plug-in connector, 300 the shunt resistance 50 by control of bridge circuit 70 (FIGS. 1 and 9) in parallel with the chamber 60 can equal the impedance of network 20 across lines 32 and 34 of connector 300.

The closure of switches SH1 through SH8 of the shunt resistance 50 of FIG. 9 can be performed by either of two means. FIG. 9 diagrams both approaches.

In FIG. 9, the shunt resistance circuit 50 is shown mechanically interconnected over lines 900 to a group of relays R1 to R8 which are selectively activated by a driver circuit 910. In a first embodiment the driver circuit includes a binary up counter which is incremented by a clock 912 over line 914.

The first embodiment operates as follows. Switches S2 and S3 in switch 30 are configured so that line 210 is connected to line 36. Low voltage pulse driver 920 delivers a reference low voltage alternating current (e.g., 0.05 volts to 1.00 volt peak-to-peak) across a bridge circuit 930 on line 922. The bridge has a reference resistor corresponding to the desired impedance of the pulse forming network 20 (in the preferred embodiment 16.5 ohms). The bridge 930 compares the impedance of the chamber/shunt combined resistance to the impedance of the referenced resistor. If the bridge is unbalanced (i.e., impedance not matched), clock 912 is activated over line 932. At this point, switches SH1 through SH8 are selectively closed by driver 910. For example, assume that switch SH1 is closed placing a 4.4 kohm resistor in parallel with chamber 60. If the resulting parallel combination of resistance does not produce a combined resistance of 16.5 ohms (the bridge is unbalanced) then SH1 opens and SH2 closes placing a 2.2 kilohm resistor in parallel with the chamber. The bridge 930 then closes both SH1 and SH2 and continues in a binary count up fashion as follows:

```
SH3
SH3, SH1
SH3, SH2
SH3, SH2, SH1
SH4
SH4, SH1
SH4, SH2
etc.
```

In the preferred embodiment, resistors have the following values:

```
R1 =    4,224 ohms
R2 =    2,112 ohms
R3 =    1,056 ohms
R4 =      528 ohms
R5 =      264 ohms
R6 =      132 ohms
R7 =       66 ohms
R8 =       33 ohms
```

Hence, as the switches SH1 and SH8 continue to close in the manner described above, the summed resistance of the chamber/shunt combination steadily decreases until it approaches a value of 16.5 ohms. The moment this summed resistance becomes less than the reference resistance in the bridge circuit 930, the voltage measured at the output of the bridge crosses zero indicating that a match has been achieved. At this point, clock 912 is deactivated and the switch closures that have achieved the impedance match are left closed. The treatment pulses can now be applied across chamber 60.

It can be seen that the bridge 930 could have a null meter for viewing by an operator who can manually set switches SH1 to SH8 of the shunt resistance 50 or it can occur automatically as described above. It is to be expressly understood that while the above disclosures connects parallel resistances, complex parallel or series impedance matching networks could be used under the teachings of the present invention to match the impedance.

In addition, switches S2 and S3 of high voltage switch assembly 30 can be controlled by computer 110 over line 113 as shown in FIGS. 1 and 9. In this configuration, the bridge 930 can deliver the bridge balance value to computer 110 over lines 113b, the computer can then directly control the clock 912 over line 113c. After the impedance is matched, the pulse treatments from the network 20 can commence.

After matching the impedance, switch S2 of the high voltage switch assembly 30 is opened, the pulse control logic 40 is given an appropriate start signal and the application of the treatment pulses across the chamber 60 commences by activating switch S2 via line 42 in FIG. 1.

What has been described is an approach to manually or automatically match the impedance of the chamber to the pulse forming network before the application of the treatment pulses.

To obtain the fastest rise times for the treatment pulses, the connecting lines 32–34 and 36–38 should be transmission lines with the same impedance as the pulse forming network 20 and the shunt/chamber combined impedance. Hence, in the preferred embodiment, these would be a 16.6 ohm line which may be obtained by using three 50 ohm coaxial lines run in parallel or an open strip line over a ground plane designed to have an impedance of 16.6 ohms.

In some uniform electrical field treatment processes, the present invention may be modified, in a second embodiment and as shown by the dotted lines in FIG. 9, to quickly match the pulse forming network 20 to the combined impedance of the shunt resistance and chamber before the delivery of each treatment pulse. If the chamber 60 is used in a flow-through mode, the concentrations of suspended vesicles or particulate matter may change, altering the impedance of the flow-through chamber from time to time. In these cases, it is necessary to change the value of the shunt resistance such that the chamber/shunt resistance is once again matched to the impedance of the drive pulse forming network 20.

In FIG. 9 the circuitry necessary to accomplish impedance matching is set forth in dotted lines. For example, in FIG. 10 a first high voltage treatment pulse 900 is applied across the chamber 60. After a predetermined time interval, T1, a second, well regulated low voltage pulse having an amplitude in the range of 0.05 to 1 volt peak-to-peak is applied immediately followed by a corresponding negative pulse of the same amplitude. The positive going pulse 910 and the negative going pulse 920 have a duration in the range of 1 to 1000 microseconds. Following the application of negative going pulse 920, a second time interval T2 is encountered before the application of the next treatment pulse 930. Under the teachings of the present invention, a single set of positive/negative pulses 910/920 could be used on a plurality of such sets as shown by 1400 in FIG. 14.

In FIG. 9, the low voltage pulses are provided by the low voltage driver 920 over line 924. During time interval T1 switch S3 of the high voltage switch 30 is activated to connect the driver 920 to the chamber 60. At the same time, switches SH1-SH8 of shunt resistance 50 are opened. The absolute value of the current flowing in line 210 as generated by pulses 910 and 920 is determined by a current sensor 940 which is delivered over line 942 into a current measuring circuit 950 for analysis by a current averager 960. The result is digitized by circuit 970 and compared to values in a look-up table 980. The current sensed at the well regulated reference voltage from pulse driver 920 will be directly proportional to the combined parallel resistance of the shunt 50 and the chamber 60. The current is referenced to as series of switch closure instructions in lookup table 980. These instructions are sent to a driver circuit 910 to select the appropriate combination of switches SH1-SH8 in shunt resistance 50 to set the necessary parallelled shunt resistance.

Look-up table 980 is a read only memory chip wherein each current value reading in the ROM chip is accompanied by a set of switch settings to be sent to the switches in the shunt resistance, SH1, SH8 in order to readjust the shunt resistance to the proper value. The values of the shunt resistor resistances may be calculated as follows. The characteristic impedance of the pulse forming network is first determined. In the case where the network is of the type that delivers rectangular wave pulses as shown in FIG. 3, the impedance, Z, is very close to the value $$Z = \text{Square root}(L/C) \quad \text{FORMULA 1}$$

The resistances in the shunt network are then, for eight resistors, 2Z, 4Z, 8Z, 16Z, 32Z, 64Z, 128Z, 256Z. Increasing the numbers of switches and resistors in the shunt resistance network 50 increases the precision with which a matching resistance may be accomplished. Conversely decreasing the number of switches and resistors decreases the matching precision.

The use of the impedance matching techniques discussed above find application for vesicular altering instrumentation applying electric fields across any chamber whether of uniform or nonuniform field generating styles for the purposes of treating suspensions of vesicles.

e. Pulse Control Logic 40

The pulse control logic 40 of FIG. 1 is in charge of the sequential operations of the present invention. It consists of specific controls, such as thumb-wheel switches, for setting the operating parameters of the apparatus. These controls which are on the operating panel of the instrument 100 are shown in FIG. 11 to include a pulse electric field strength control 1100, a number of pulses control 1110, an interval between pulses control 1120 and a pulse length control 310.

In one preferred embodiment, the field strength control 1100 is adjustable in the range 0-10 Kilovolts/Centimeter, the number of pulses control 1110 can be set from 1 to 99, the pulse length control 310 can be set from 1-10 microseconds and the interval between pulses control 1120 can be set from 0.1-10.0 seconds. In this embodiment, the pulse forming network 20 uses the configuration as shown in FIG. 3 to output fast rise time rectangular pulses of FIG. 4.

As shown in FIG. 11 and with reference to FIG. 1, the electric field control 1100 sets the amplitude of the high voltage power supply over line 44, the pulse length control 310 sets the switches SP1 to SP10 of FIG. 3 in the pulse forming network 20 over line 46, the pulse interval control 1120 and the number of pulses control 1110 operates the high speed switch assembly of FIG. 2 over line 42. Likewise, the pulse logic circuit 40 can be optionally controlled by computer 110 over lines 114 to automatically control the above settings.

In operation, one could quickly set the apparatus to produce 8 pulses of six kilovolt/centimeter field intensity with a pulse interval of one second and a pulse length of five microseconds. Setting the pulse length to five microseconds would close switches SP1, SP2, SP3, SP4, SP5 in the pulse forming network 20 of FIG. 3. With these switches closed, setting the field strength to three kilovolts/centimeter would charge up capacitors C1, C2, C3, C4, C5, and Cll to a voltage of three kilovolts. Setting pulse number and pulse interval would preset timers in the control logic that determine when the closures of a high voltage gas filled relay S2 will happen, namely eight times with durations of one second between closures.

When the "Process Start" button 1140 is engaged, the pulse logic 40 first connects the bridge 70 to the chamber and matches load impedance as explained above. When impedance matching has been performed, the pulse logic 40 signals the interval and pulse number controls to close the high voltage switch S2 at the preset number of times with the preset interval.

Each time switch S2 closes in this embodiment, a 3 kilovolt pulse will be delivered to the pulse chamber as it is the nature of this network to deliver a rectangular pulse of one-half the charge voltage into a resistance equal to the network characteristic impedance. So, a pulse of three kilovolts would be impressed across pulse chamber 60. The pulse chamber 60 in this embodiment has a spacing of 0.5 centimeters between parallel plate electrodes. The resultant field in the chamber at the desired pulse voltage would then be:

$$3 \text{ Kvolts}/0.5 \text{ cm} = 6 \text{ kvolts/cm} \qquad \text{FORMULA 2}$$

It is to be expressly understood that while a preferred embodiment for the pulse logic 40 has been presented that other suitable approaches could be used such as direct control by computer 110 could be utilized under the teachings of the present invention. In addition, the intervals between each of the pulses as can be individually varied (e.g., 1 second between pulses 1 and 2 and 2 seconds between pulses 2 and 3, etc.).

f. Chamber 60

Figure 13:
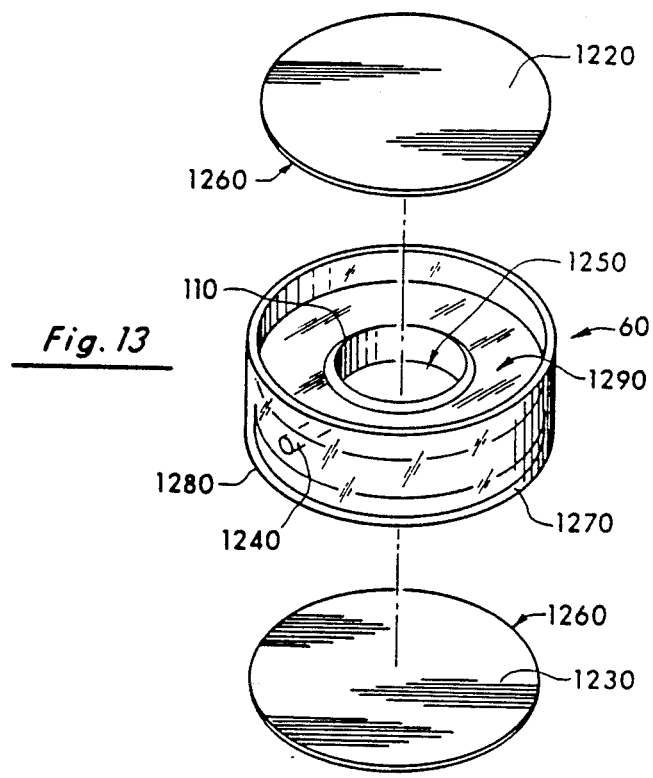

In FIGS. 12 and 13 the electroporation chamber 60 of the present invention is shown. The chamber 60 has two opposing electrodes 1220 and 1230 and a small formed hole 1240. As shown in FIG. 13, the chamber 60 has a formed annular region or cavity 1250 which comprises the actual electroporation chamber.

In FIG. 13, each of the electrodes 1220 and 1230 are identical and are formed of conductive material such as copper, brass, or steel. The electrodes 1220 and 1230 are plated with an inert noble metal such as gold or platinum. The chamber 60 also incorporates a holder 1270 which comprises an outer collar 1280 and an inner ring 1290. The collar 1280 and the ring 1290 are integral elements of the chamber formed of dielectric material such as polycarbonate in the preferred embodiment or other suitable plastics, ceramic, or glass. Each electrode 1220, 1230 is designed to press-fit into the inner surface of the collar 1280. The diameter of each electrode is slightly greater than the inside diameter of the collar 1280 such as 0.002 inches.

The above chamber is designed as a non-flow-through chamber. However, it is to be expressly understood that a second formed hole, not shown, in the inner ring 1290 opposing the first hole 1240 could be inserted and that the fluid could be pumped into and out from the chamber 1250.

Figure 14:
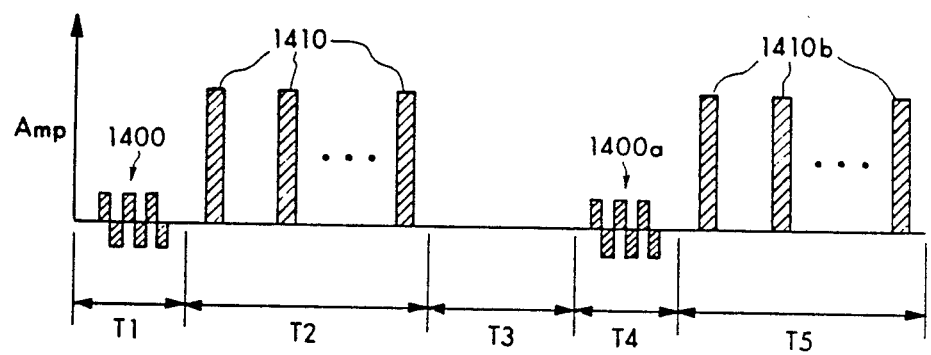
FIG. 14 sets forth an operational sequence for treating solutions in a flow-through chamber of the present invention.

For a flow-through chamber, the sequence of operation of the present invention is shown in FIG. 14. In time interval T1, the chamber 60 holding a suspension containing vesicles first has its impedance matched according to the bridge circuit 70 shown in FIG. 9. The pulses 1400 represent a series of low voltage pulses necessary to match the impedance as discussed above. After impedance matching occurs, the application of multiple treatment pulses 1410 occur during time interval T2. Upon completion of the multiple treatment pulses 1410, the treated suspension is then pumped by pump 140 (FIG. 1) from the chamber 60 during time interval T3. A new suspension is delivered into chamber 60 and the impedance is matched by pulses 1400a during time interval T4. Finally, during time interval T5 a second set of treatment pulses 1410b are applied. This process continues as the fluid is pumped through chamber 60.

g. Multiple Pulsing of Flow-Through Chamber

In FIG. 7, the application of the multiple pulse technique of the present invention is applied to a flow-through chamber. In FIG. 7, a rectangular shaped flow-through chamber 700 is shown. The chamber 700 has opposing parallel electrodes 710 and 720 separated by insulated sidewalls 730. The treatment pulses are applied to the electrodes 710 and 720. The solution flows into the chamber as shown by arrow 740 and leaves the chamber as shown by arrow 750.

Assume that "n" pulses constitute a series of multiple pulses which are applied to the chamber 700. The chamber is divided into "n" flow volumes as indicated in FIG. 7 as V1–Vn. The flow rate for the suspension flowing into the chamber 700 is such that during the application of the first pulse of "n" pulse to the chamber 700, the entire volume of the chamber is treated with the first pulse. The flow rates are designed, however, so that at the time the second pulse of the "n" pulses is applied, the suspension contained in volume V1 (when the first pulse was applied) has traveled to occupy volume V2. At this point in time, volumes V2–Vn have all received two applications of treatment pulses whereas the suspension in volume V1 has received only one treatment pulse application. During the third time interval, the solution continues to move so that when the third treatment pulse is applied, the suspension of volume V2 (at the time of the second pulse) has moved to volume V3. After the application of the third treatment pulse, volumes V3–Vn have now received three treatment pulses, volume V2 has received two treatment pulses, and volume V1 has received one treatment pulse. This process continues until the suspension originally in volume V1 (at the time of the first pulse) occupies volume Vn for the application of the "nth" treatment pulse so that as the suspension continuously flows through the chamber 700 and leaves at outlet 750, each of the volumes has received "n" treatment pulses.

The flow-through multipulsing system of FIG. 7 is defined for any series of multipulses. For example, if n equals the number of pulses, then the chamber 700 has its volume divided by n (i.e., V/n) and the flow rate of the suspension through the chamber as shown by arrows 740 and 750 is adjusted to move the suspension as discussed above. In this fashion, substantial quantities of suspensions containing vesicles can be continuously pulsed.

Figure 8:
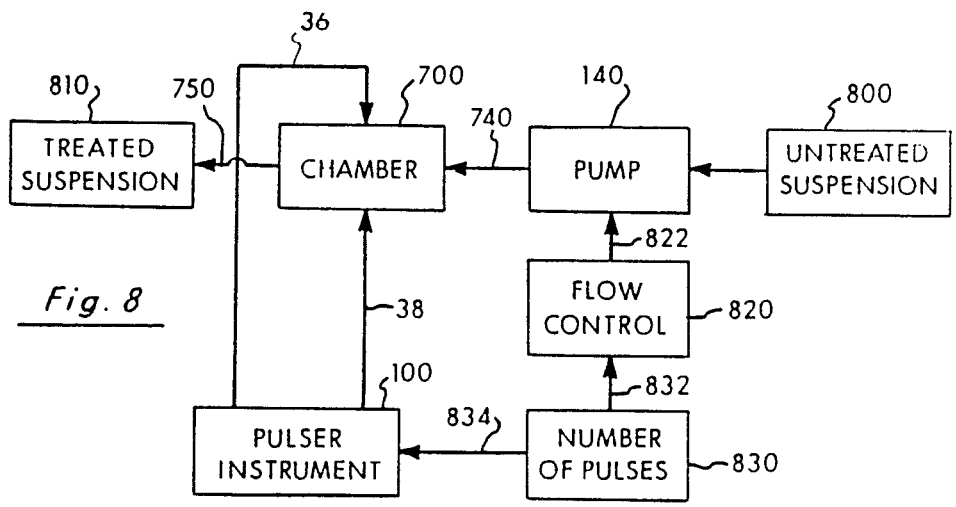
FIG. 8 is a block diagram of a multiple pulsing technique of the present invention using the chamber of FIG. 7.

In FIG. 8, a system for accomplishing multiple pulsing in a flow-through chamber is set forth to include the chamber 700 interconnected with the instrument 100 of the present invention for the delivery of treatment pulses over lines 36 and 38. A pump 140 delivers the suspension from a source 800 into the chamber 700 through lines 740 and, after delivery, over lines 750 to a destination 810. The pump 140 continuously pumps the fluid through the chamber 700. The rate of flow, however, is controlled by a separate flow control 820 which over lines 822 controls the rate of flow for the pump 140. The flow control 820 is under direct supervision by circuit 830 over lines 832. Hence, if "n" pulses are selected at 830, the rate of flow control 820 is suitably adjusted to set pump 140 at the proper flow rate described above for FIG. 8. Likewise, the number of pulses in circuit 830 over line 834 controls the number of multiple pulses delivered by the instrument 100.

It is to be expressly understood that variations to the circuitry set forth in FIG. 8 could be made which, under the teachings of the present invention, perform the effect described above for FIG. 8.

The following examples set forth the advantages of using multiple pulses over the use of a single pulse for vesicular alterations.

EXAMPLE 1

Effects of Dividing a Single Pulse into Multiple Pulses

This example demonstrates the beneficial advantage of delivering a multiplicity of uniform electric field pulses to the chamber 60 containing biological cells in suspension. Increasing the number of pulses, while maintaining the cumulative pulse duration constant, resulted in greater alteration of the vesicle membrane as demonstrated by the increased release of hemoglobin through electroporation of the erythrocyte membrane.

A 6% volume:volume (v:v) suspension of human erythrocytes was prepared in HBS (HEPES buffered saline; 10 mM HEPES, 0.15 M NaCl) for this example. The vesicle suspension was chilled to four degrees centigrade and one milliliter volumes were transferred to a prechilled electroporation chamber with a 0.5 cm space between electrodes. The preparation was then subjected to uniform electric fields of 6 Kv/cm for the times specified in Table 1. The rectangular wave pulse lengths, applied at 6 second intervals, and the numbers of pulses were adjusted so that the total pulse duration remained constant at 40 microseconds. The total energy was determined by measuring the pulse voltage, current, and pulse length on a Tektronix 2450 digital storage oscilloscope. The rise time of each pulse was less than 200 nanoseconds. As noted, the total energy delivered to the chamber was constant for each series of pulses, and equal to 8.9 Joules. The uniform electric field impressed across the electrodes of chamber 60 is 6 kV/cm.

The vesicle suspension was incubated on ice for 5 minutes to allow hemoglobin egress, then centrifuged at 12,000 X g for 5 minutes to pellet the erythrocytes and ghosts. The hemoglobin remaining in solution was determined after appropriate dilution by its Soret absorbance at 415 nm. Comparison was made to total hemoglobin found in water-detergent lysates to determine the percent of hemoglobin released by each electroporation. The results are presented in tabular form in Table I and in graphical form in FIG. 15.

TABLE I

| | Effect of Multiple Pulses on Electroporation Efficiency | | | |
|---|---|---|---|---|
| NO. OF PULSES | PULSE DURATION ($\mu$sec) | CUMULATIVE DURATION ($\mu$sec) | SORET ABSORBANCE | HEMOGLOBIN RELEASED (%) |
| 1 | 40 | 40 | 1.016 | 22.9 |
| 2 | 20 | 40 | 1.477 | 32.7 |
| 4 | 10 | 40 | 1.954 | 44.0 |
| 8 | 5 | 40 | 2.750 | 61.9 |

Figure 15:
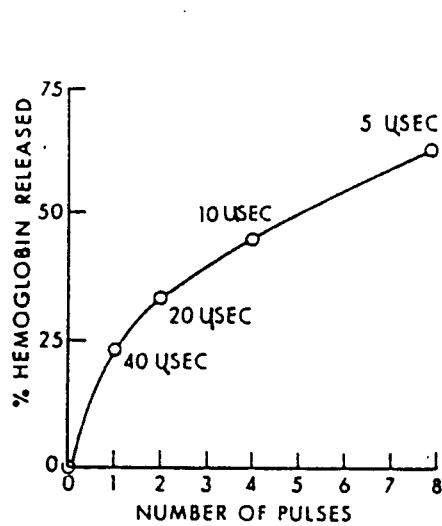
FIGS. 15, 16, 17, 18 and 19 set forth the graphical results of Examples I, II, and III.

In FIG. 15, the abscissa represents the number of pulses delivered to each suspension while the ordinate indicates the percent of vesicular hemoglobin released into the medium following treatment. The numbers above each point indicate the individual pulse length of the imposed field.

It is clearly apparent upon examination of the data presented in both Table I and FIG. 15, that division of an electrical pulse into a multiplicity of pulses is much more effective than a single pulse for optimizing electroporation as evidenced by hemoglobin release from erythrocytes. These results are consistent with the concept that the molecular transitions which result in membrane electroporation are responsive to the imposition of rapidly changing electrical fields. Furthermore, imposition of a multiplicity of such rapid rise time pulses yields the unexpected and beneficial effect of greatly enhancing the efficacy of the electrical field for membrane alteration.

EXAMPLE 2

Comparison of the Effects Between Single Pulse and Multiple Pulses

This example further demonstrates the beneficial advantage of a multiplicity of pulses over a single pulse of the same field intensity and pulse duration. Providing a series of multiple pulses in comparison to a single pulse with equal cumulative pulse duration results in greater alteration of the vesicle membrane as demonstrated by the increased release of hemoglobin through electroporation of the vesicle membrane.

A 6% (v:v) erythrocyte suspension was prepared as described in Example 1. One milliliter aliquots of the suspension were transferred to chilled chambers, as in Example 1, and subjected to uniform field electrical discharges as in Example 1.

The experimental treatments were divided into two groups. For the first group, the pulse duration of a single electrical pulse was varied. For the second group, the pulse duration was fixed at 5 microseconds while the number of pulses was varied such that the cumulative pulse duration for the multiple pulse group could be compared to the pulse durations in the single pulse group. For the multiple pulse group, the interval between pulses was 6 seconds. The results are summarized in Table II and FIG. 16.

TABLE II

| COMPARISON OF ELECTROPORATION BY SINGLE PULSE AND MULTIPULSE EQUIENERGETIC ELECTRIC FIELDS | | | | |
|---|---|---|---|---|
| NO. OF PULSES | INDIVIDUAL PULSE DURATION ($\mu$sec) | CUMULATIVE PULSE DURATION ($\mu$sec) | TOTAL ENERGY (JOULES) | HEMOGLOBIN RELEASED (%) |
| (First Group) | | | | |
| 1 | 5 | 5 | 1.1 | 12.5 |
| 1 | 10 | 10 | 2.2 | 21.1 |
| 1 | 15 | 15 | 3.3 | 24.4 |
| 1 | 20 | 20 | 4.4 | 25.4 |
| 1 | 30 | 30 | 6.7 | 29.2 |
| 1 | 40 | 40 | 8.9 | 31.2 |
| (Second Group) | | | | |
| 1 | 5 | 5 | 1.1 | 12.5 |
| 2 | 5 | 10 | 2.2 | 26.2 |
| 3 | 5 | 15 | 3.3 | 32.4 |
| 4 | 5 | 20 | 4.4 | 36.7 |
| 6 | 5 | 30 | 6.7 | 45.2 |
| 8 | 5 | 40 | 8.9 | 52.0 |

Figure 16:
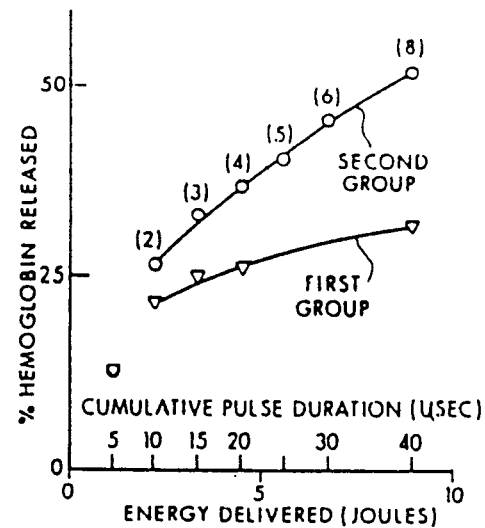

The dual scaled abscissa of FIG. 16 represents both the cumulative pulse duration (upper scale) and the energy delivered to each of the vesicle preparations (lower scale) while the ordinate represents the percent hemoglobin released from the vesicles following 5 minute incubations at four degrees centigrade. The number associated with each point on the upper curve of FIG. 16 represents the number of pulses delivered to each sample. Several conclusions may be drawn after examination of Table II and FIG. 16. First, the application of multiple pulses (Second Group) substantially improves membrane alterations as evidenced by hemoglobin release when compared to the application of a single comparable pulse (First Group). Second, increased pulse duration increases the percent hemoglobin released for both the first and the second group. Third, under these experimental conditions, the amount of energy delivered to the chamber is directly proportional to the pulse duration. Therefore, the amount of energy expended for a given vesicular alteration is significantly reduced when multiple pulses are delivered to the suspension rather than a single pulse. For example, as can be seen in Table II, a single pulse of 40 microseconds releases 31.2% of the cellular hemoglobin while three 5 microsecond pulses for a total cumulative pulse duration of 15 microseconds release a virtually identical percentage. However, the multiple pulse treatment required only 37% (3.3/8.9)*100 of the energy required for the single pulse treatment. Therefore, delivery of a multiplicity of controlled pulses allows the use of considerably shorter cumulative pulse durations to achieve the desired results, thereby significantly reducing the Joule heating of the chamber and the undesired effects associated with such heating.

The effects of enhanced membrane alteration by a multiplicity of electric pulses is further shown in Table III below.

TABLE III

PERCENT IMPROVEMENT IN HEMOGLOBIN RELEASE PRODUCED BY MULTIPLE PULSES

| CUMULATIVE PULSE DURATION ($\mu$sec) | TOTAL ENERGY (JOULES) | (FIRST GROUP %) LESS (SECOND GROUP %) | IMPROVEMENT IN HEMOGLOBIN RELEASE (%) |
|---|---|---|---|
| 10 | 2.2 | 5.1 | 19.5 |
| 15 | 3.3 | 8.0 | 32.8 |
| 20 | 4.4 | 11.3 | 44.5 |
| 30 | 6.7 | 16.0 | 54.8 |
| 40 | 8.9 | 20.8 | 66.7 |

From Table III, it is further apparent that dividing a single electrical pulse into multiple pulses enhances the extent of membrane alteration as evidenced by hemoglobin release. For example, a single 40 microsecond pulse releases 31.2 percent of the cellular hemoglobin while eight 5 microsecond pulses release 52 percent. The difference is 20.8 percent. This results in a 66.77 percent improvement (20.8/31.2) in the efficiency of hemoglobin release.

Figure 17:
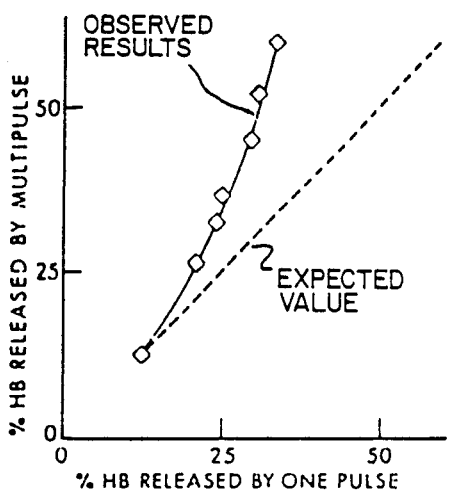

The improvement in efficiency of electroporation can further be appreciated by the graphical depiction of the data in Table III (FIG. 17. The abscissa of FIG. 17 represents the percent hemoglobin released from erythrocytes exposed to a single pulse while the ordinate represents the percent hemoglobin released by multiple pulses. The cumulative pulse duration is shown above each of the points on the solid line in FIG. 17. In the absence of these teachings, one skilled in the art of electroporation would expect no difference between the treatments. The broken line indicates this anticipated 1:1 relationship. Quite unexpectedly, the application of multiple pulses improves the efficiency of hemoglobin release, as evidenced by the upward curvature of the solid line.

The beneficial effects of these findings are important for vesicular alterations. For example, improved electroporation permits more uniform access to the interior of vesicles for the purposes of removal or insertion of substances. Furthermore, the desired degree of vesicular alteration may be attained through the application of considerably less energy, thereby reducing the undesired effects of (e.g., Joule heating) the process on vesicles in suspension. Lastly, although a maximum of 8 pulses were used in this example, it is believed that division of a single electric pulse into even more pulses will result in further improvement in electromanipulation and cell viability. This conclusion is based upon extrapolation of the data illustrated in FIGS. 15 through 17.

EXAMPLE 3

Effects on Vesicular Alterations by Varying the Interval Between Pulses

This example demonstrates the importance of selecting the optimum interval between pulses when a multiplicity of pulses is used for vesicular alteration. Varying the time interval between pulses in a series of pulses significantly effects the alteration of the membrane as demonstrated by the increased release of cellular hemoglobin through electroporation of the vesicle membrane. For this example, one milliliter erythrocyte suspensions (6%, v:v) were subjected to 8 rectangular electrical impulses, each with a field intensity of 6 Kv/cm, a duration of 5 microseconds and a rise time less than 200 nanoseconds. The energy delivered to each vesicle preparation was 8.9 Joules. The interval between pulses was varied between 0.1 and 10 seconds and the hemoglobin release was determined as described in Examples I and II. The results of this experiment are presented in Table IV and are graphically shown in FIG. 18.

TABLE IV

EFFECT OF THE INTERVAL BETWEEN PULSES ON HEMOGLOBIN RELEASE FROM ERYTHROCYTES

| INTERVAL (sec) | LOG INTERVAL | MEAN HEMOGLOBIN RELEASE (%) | NO. OF OBSERVATIONS | STANDARD DEVIATION |
|---|---|---|---|---|
| 10 | 1.00 | 44.3 | 3 | 1.7 |
| 3 | 0.48 | 41.2 | 3 | 0.5 |
| 1 | 0.00 | 33.4 | 3 | 0.9 |
| 0.3 | −0.52 | 27.4 | 3 | 1.6 |
| 0.1 | −1.00 | 24.9 | 3 | 2.7 |

Figure 18:
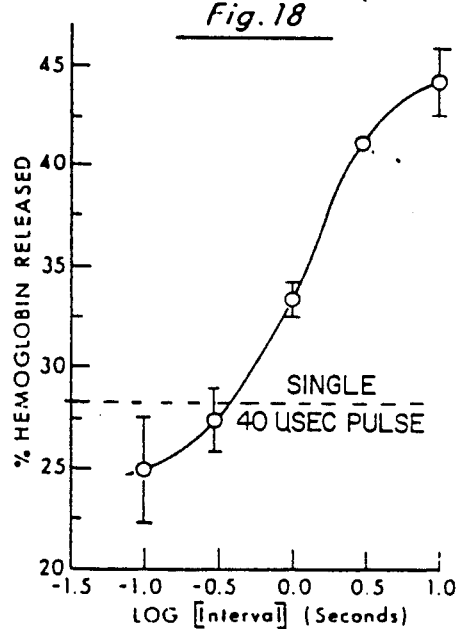

In FIG. 18, the abscissa indicates the log of the interval between pulses while the ordinate indicates the percent hemoglobin released after 5 minutes incubation at four degrees centigrade. The horizontal broken line indicates the percent hemoglobin released following a single, 40 microsecond pulse (28%).

Figure 19:
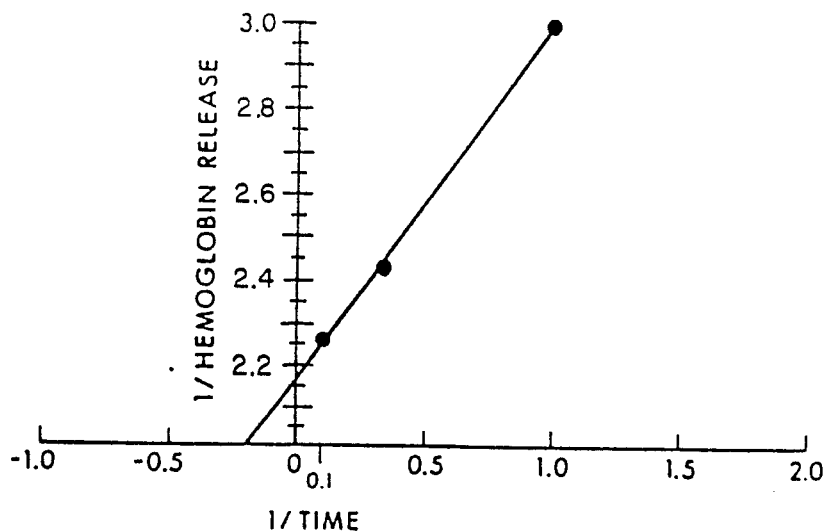

In Table V, the Langmuir isotherms are generated for intervals of 0.1, 0.33 and 10 seconds and are plotted in FIG. 19.

TABLE V

| LANGMUIR ISOTHERMS | |
|---|---|
| 1/TIME (SEC-1) | 1/(HB RELEASED) |
| 1.00 | 2.99 |
| 0.33 | 2.43 |
| 0.10 | 2.26 |

Referring to the data presented in Tables IV and V and as shown in FIGS. 18 and 19, it is apparent that the effect on hemoglobin release of a multiplicity of electrical pulses depends significantly on the interval between pulses. For the release of hemoglobin from erythrocytes, intervals shorter than about 0.9 seconds/pulse are less effective than a single pulse of equivalent cumulative pulse duration. This lower interval limitation is not surprising since Sowers (U.S. Pat. No. 4,622,302) recites that frequencies in the range of 2 to 10 Hz cause vesicle aggregation and fusion, thus one would not expect much hemoglobin release at intervals corresponding to those frequencies. What is surprising is that frequencies lower than those recited by Sowers improve membrane alterations so dramatically (i.e., intervals between 0.9 seconds/pulse and 10 seconds/pulse). There is no relevant art which has revealed this phenomenon. Accordingly, this example teaches the unexpected fact that selection of the optimum interval between electrical pulses is important to maximize the efficacy of the multiple pulse phenomenon.

Because erythrocytes possess a unique shape and size, an optimum range of intervals between 0.9 and 10 seconds was observed. For other vesicle types which differ significantly in size, shape, and internal structure, the number of pulses and the interval between pulses for optimum vesicular alteration will have to be determined for each vesicle type using the procedures and methods set forth in this invention and, therefore, the range may or may not fall within the range of intervals observed for erythrocytes. If one applies similar multiplicity of pulses to vesicles such as bacteria or yeasts, for instance, the number of pulses and interval between pulses will have to be optimized as taught for erythrocytes in this example. In like manner, multiple pulses which optimally alter nucleated vesicles will be found to be characteristic to those vesicles using the procedures taught herein for erythrocytes.

SUMMARY OF EXAMPLES I, II AND III

The results of Example I, II and III may be summarized as follows:

EXAMPLES I and II

For a given cumulative pulse duration applied to the chamber, increased vesicular alteration is achieved by increasing the number of pulses.

EXAMPLE III

Varying the time interval between the pulses in a series having a fixed number of pulses effects the degree vesicular alteration.

Therefore, the degree of electromanipulation as demonstrated by the release of cellular hemoglobin through electroporation of human erythrocytes, can be controlled by varying the number of pulses and by varying the time interval between the pulses. The above examples directly support a range of pulses for erythrocytes from two to eight and a time interval for 0.9 sec/pulse to 10 sec/pulse for hemoglobin release of erythrocytes. In principle, for other vesicle types and other types of vesicular alterations, other optimum ranges would have to be established under the teachings of this invention.

Therefore, this invention teaches that the degree of electromanipulation of any membranous vesicular structure will be likewise controlled by exposure to a multiplicity of electric pulses when exposed to sufficient field intensities with appropriate pulse intervals. Such macromolecular structures include, but are not limited to, vesicle membranes, vesicle walls, cellular elements such as lysosomes, golgi structures, endoplasmic reticular structures, mitochondria, choloroplasts, nuclear envelopes, lipid bilayers, lipoproteinaceous structures, glycoprotenaceous structures, nuceloproteinaceous structures such as chromation or ribosomes, and proteins or polypeptides.

EXAMPLE 4

Improvement of Sucrose Loading into Erythrocytes by Multiple Pulses

Example 4 sets forth the improvement in vesicular alteration by delivering multiple pulses for the purpose of loading substances into vesicles which are otherwise impermeable to those substances. Application of a multiplicity of pulses to a suspension of erythrocytes results in a significant improvement in the uptake of radioactively labeled sucrose by the cells when compared to a single electrical pulse of comparable cumulative pulse duration.

Figure 24:
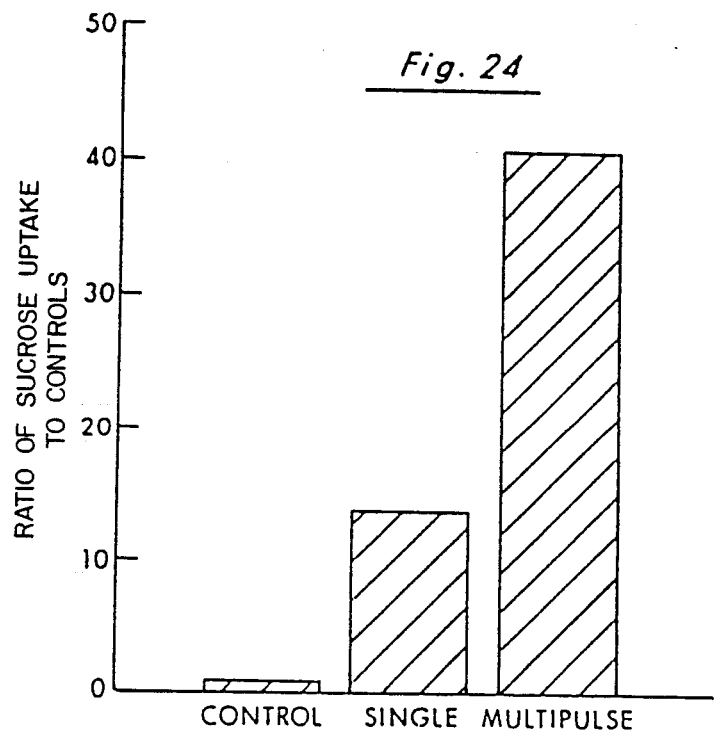
FIG. 24 sets forth the graphical results of Example IV.

For the purpose of loading erythrocytes with radioactive sucrose, erythrocytes were suspended (25%, v:v) in a solution of HBS, unlabeled sucrose, and radioactively labeled sucrose. One milliliter samples were subjected to either a single 40 microsecond pulse or 8 five microsecond pulses and incubated on ice for 5 minutes to permit uptake of the sucrose into the cells. The cells were resealed following sucrose loading by incubating at 37 degrees Centigrade for 30 minutes. They were then washed extensively in HBS containing sucrose and lysed. The lysates were bleached with hydrogen peroxide and counted for radioactivity in a liquid scintillation counter. The molar amount of sucrose incorporated into the cells was calculated from the radioactivity found and the specific activity (radioactivity/micromole sucrose). The results of this experiment are presented in Table VI and the ratio of sucrose uptake by electromanipulated erythrocytes to controls is shown in FIG. 24.

TABLE VI

COMPARISON OF SUCROSE LOADING INTO ERYTHROCYTES TREATED BY SINGLE AND MULTIPLE PULSES

| SAMPLE DESCRIPTION | # PULSES | CUMULATIVE PULSE ($\mu$sec) | SUCROSE LOADED CELLS ($\mu$moles) | RATIO OF SUCROSE UPTAKE TO CONTROL |
|---|---|---|---|---|
| Control-1 | 0 | 0 | 0.062 | |
| Control-2 | 0 | 0 | 0.072 | |
| Average | 0 | 0 | 0.067 | 1.0 |
| Single Pulse-1 | 1 | 40 | 0.963 | |
| Single Pulse-2 | 1 | 40 | 0.890 | |
| Average | 1 | 40 | 0.926 | 13.8 |
| Multi-Pulse-1 | 8 | 40 | 2.714 | |
| Multi-Pulse-2 | 8 | 40 | 2.747 | |
| Average | 8 | 40 | 2.731 | 40.8 |

Examination of the data presented in this example reveals that the application of multiple pulses improves the uptake of sucrose by erythrocytes threefold over a single pulse of equal duration, consistent with the principles taught by the hemoglobin release examples. Accordingly, the application of multiple pulses is much more effective than an equivalent single pulse for controlling both release (Examples 1–3) and loading (Example 4) of materials across otherwise impermeable vesicular membranes.

EXAMPLE 5

Electrostructuring and Creation of Blebs

Example 5 sets forth a new Vesicular alteration discovered through the use of the instrument 100 of the present invention. Unlike electrofusion, electroporation or electropermeation, this alteration of membrane morphology must be described through the coining and defining of new words. The new alteration may be called electroformation or electrostructuring of vesicle membranes (FIGS. 20–23). FIGS. 20–23 are photographs of cell membranes obtained through ultra-rapid freeze fracture techniques.

Figure 20:
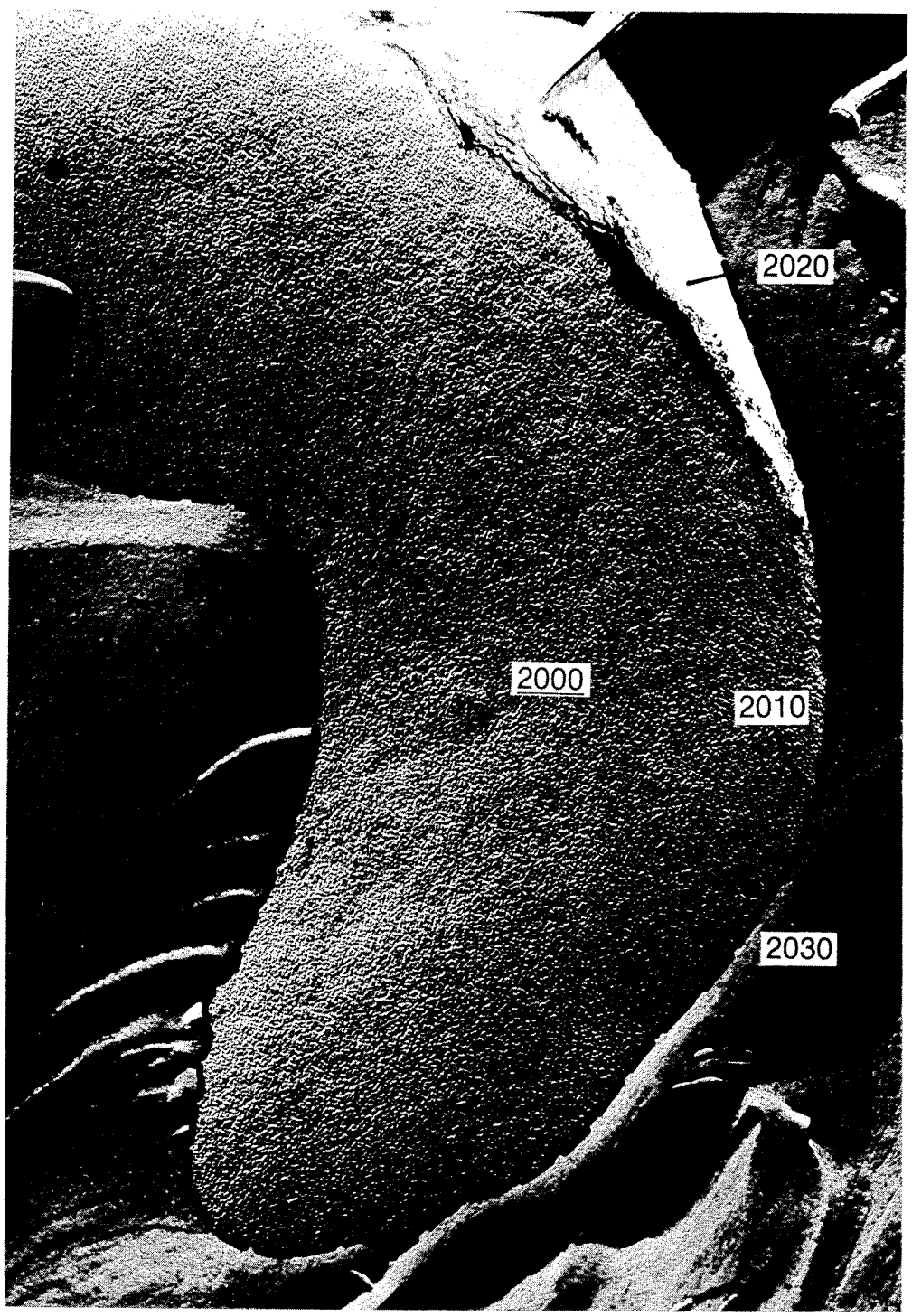
FIGS. 20 and 21 are photographs showing electrostructuring of vesicle membranes as discussed in Example V.

FIG. 20 illustrates a control cell not subjected to electromanipulation by the present invention. This shows a human erythrocyte cell 2000 having a membrane 2010. An upper portion 2020 of the membrane 2010 is shown in FIG. 20. Ice 2030 results from the freeze fracture technique.

Figure 21:
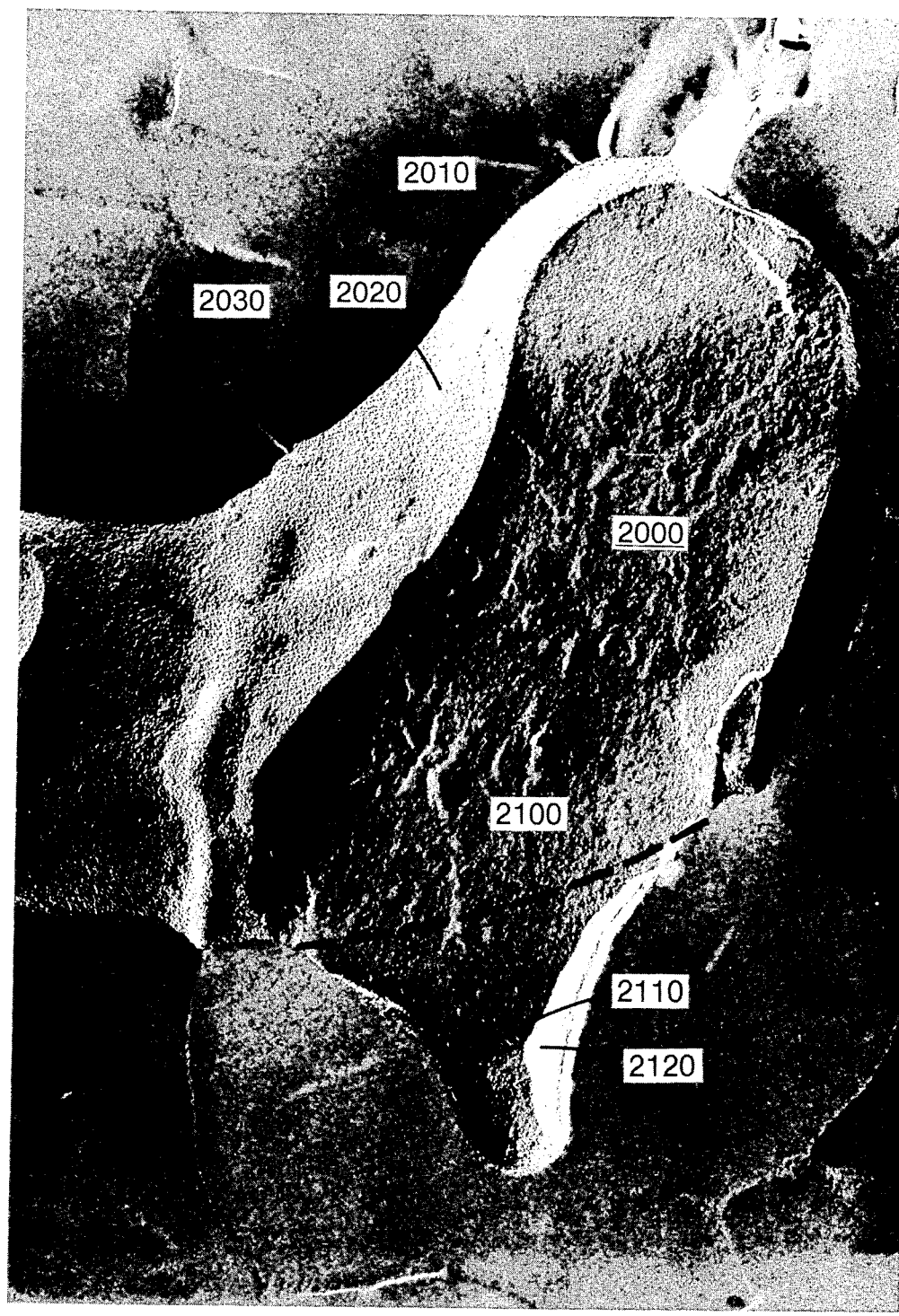
Figure 22:
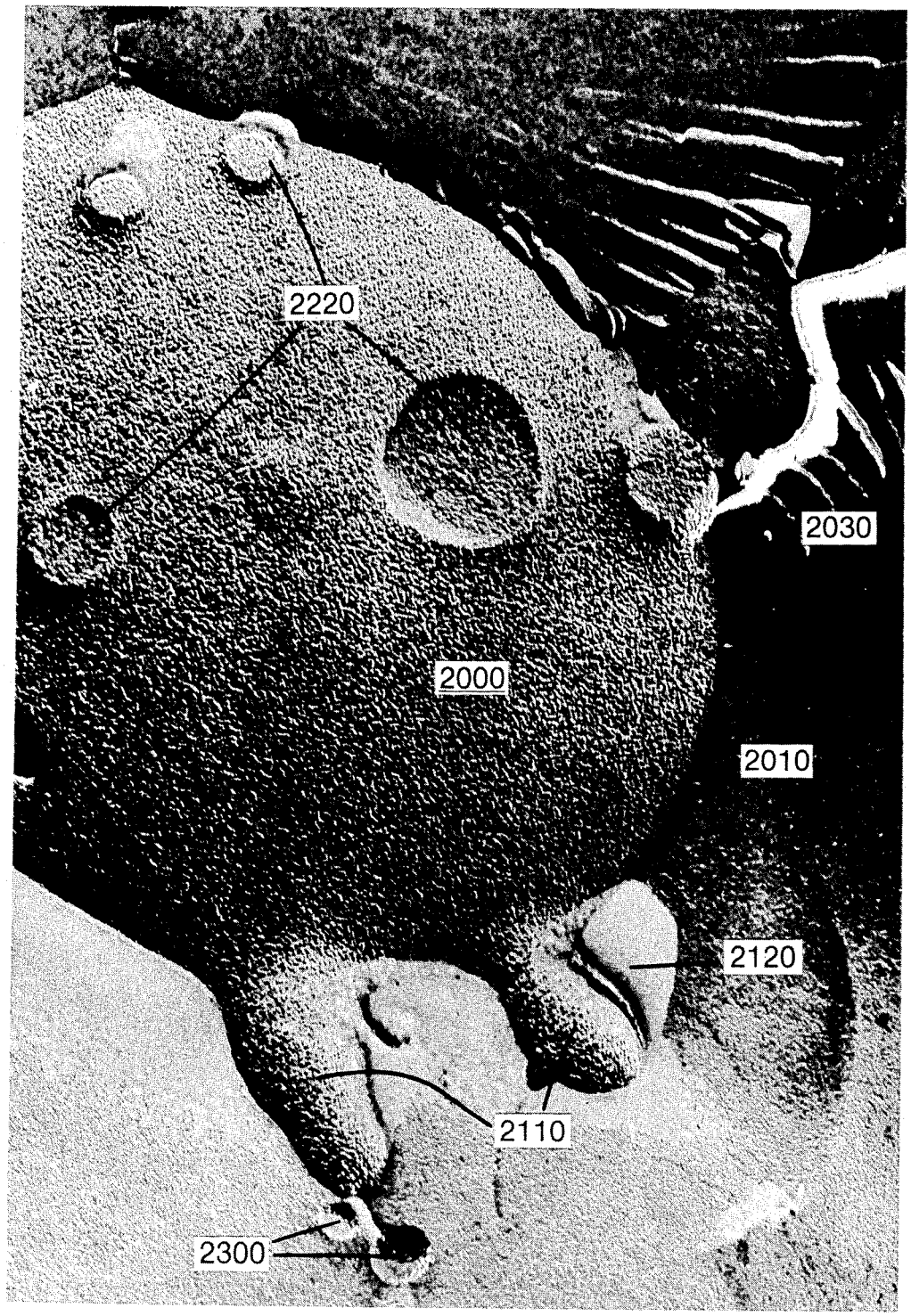
FIGS. 22 and 23 are photographs showing the creation of vesicular fragments.
Figure 23:
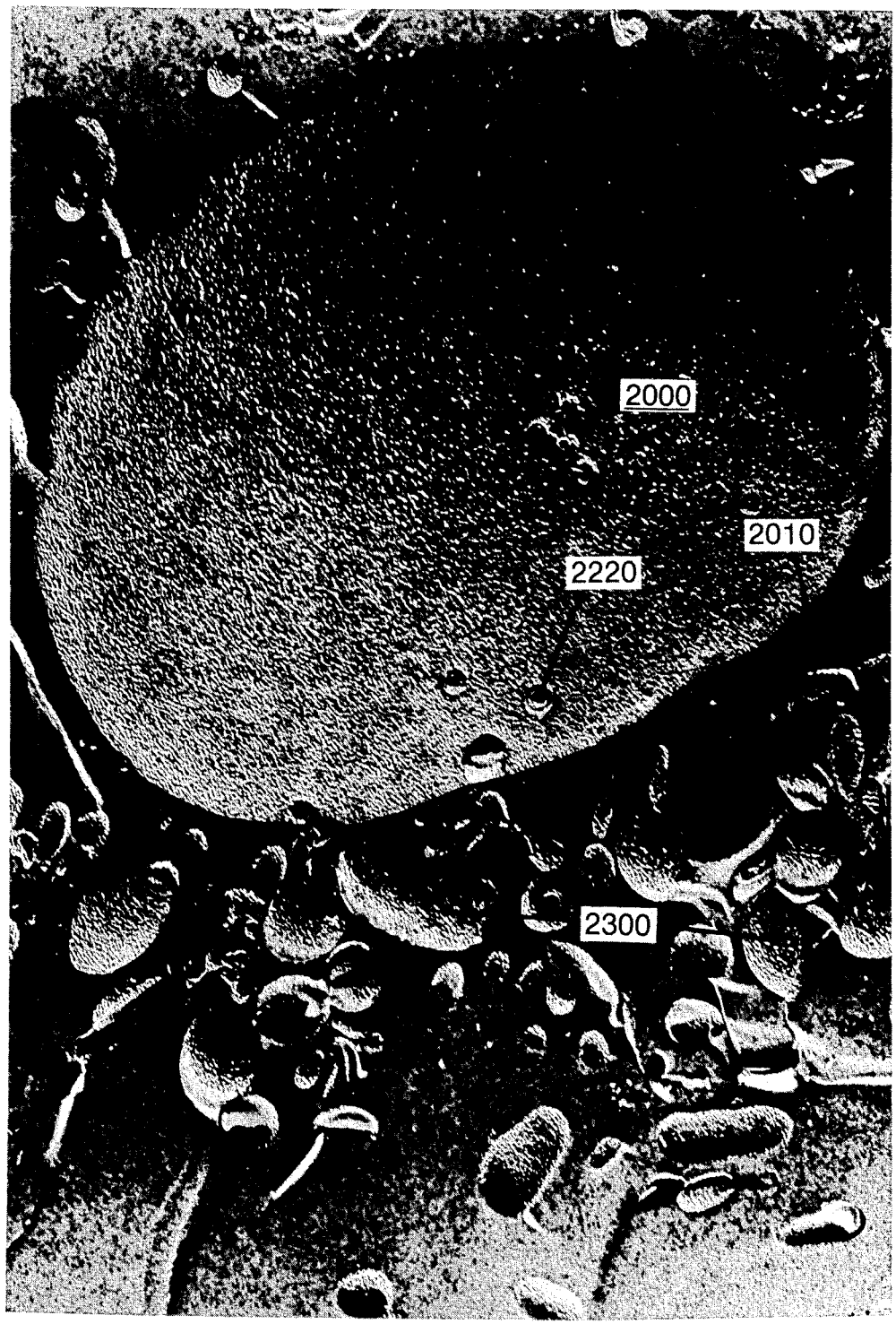

FIGS. 21 and 22, reveal the existence of electrically induced vesicular entities, "blebs" 2110, on the surface of erythrocytes. Again, the membrane portion 2120 is shown on blebs 2110. FIGS. 22 and 23 also reveals the existence of electrically induced vesicular fragments 2300 which originated from the erythrocyte membrane surface. The conditions which were used to produce these electrostructures are listed in Table VII:

TABLE VII

CELL SUSPENSION TREATMENT CONDITIONS PRIOR TO FREEZE-FRACTURE ELECTRON MICROSCOPY

| FIGURE | ILLUS-TRATING | # PULSES | VOLTAGE | TOTAL ENERGY (JOULES) | PULSE WIDTH ($\mu$SEC) |
|---|---|---|---|---|---|
| 20 | CONTROL | NONE | 0 kV/cm | 0.0 | 0 |
| 21 | BLEB | 1 | 8 kV/cm | 1.7 | 5 |
| 22 | DETACHING FRAGMENTS | 8 | 8 kV/cm | 13.6 | 5 |
| 23 | FRAGMENTS | 8 | 8 kV/cm | 13.6 | 5 |

The cells found in FIGS. 22 and 23 show the creation of vesicular fragments 2300 from a cell 2000.

Blebbing has often been observed when cells are chemically or biologically perturbed; however, these features have not heretofore been demonstrated to result from the application of electric fields. The ability to form and alter blebs through electrical means as set forth in this teaching will greatly facilitate research in the area of vesicular ultrastructure, as can be readily appreciated by one skilled in the relevant art. In addition vesicular fragments when detached from the parent cell, can serve as naturally derived "liposomes" and may be used for many of the same purposes as artificially generated liposomes. These natural vesicles possess many salutary biochemical characteristics not shared by their artificial analogs such as surface distribution of natural proteins, lipid compositions, and carbohydrate distribution which will greatly facilitate their utility in biomedical and biological applications. Their utility can be further enhanced by preloading the parent cells with a desired agent, then forming the natural liposomes, whereupon the vesicles will contain appreciable quantities of the material preloaded into the parent cell. These loaded natural liposomes can then be used for any purpose which artificial liposomes are currently employed including microinjection, genetic manipulation, and like purposes. The potential benefits to research, medicine, and industry of such naturally derived vesicles can readily be appreciated by one skilled in the appropriate art.

It is to be expressly understood that the claimed invention is not to be limited to the description of the preferred embodiment but encompasses other modifications and alterations within the scope and spirit of the inventive concept.

I claim:

1. An instrument for electrically altering the membranes of vesicles in a suspension in order to perform vesicular alteration and electrostructuring of said membranes, said instrument comprising:

means for supplying voltage, means selectively connected to said supplying means for forming one or a series of treatment pulses, a pair of electrodes, means receptive of said vesicles in said suspension for holding said suspension between said pair of electrodes, means connected to said forming means for selectively delivering each said treatment pulse from said forming means across said electrodes in said holding means, means connected in parallel across said electrodes for matching the impedance of said holding means containing said suspension to the impedance of said forming means, means connected to said matching means and selectively connecting to said electrodes in said holding means before the delivery of said treatment pulses from said delivering means for determining whether the impedance of said holding means matches the impedance of said forming means, said connecting means changing the impedance of said matching means until said holding means impedance matches said forming means impedance.

2. The instrument of claim 1 in which said forming means comprises a plurality of separate pulse forming networks wherein each pulse forming network forms a different shaped treatment pulse or treatment packet of pulses.

3. The instrument of claim 2 wherein each of said pulse forming networks reside on a separate module which plugs into said instrument.

4. The instrument of claim 1 wherein said pulse forming network comprises means for selectively varying the duration of said treatment pulses.

5. The instrument of claim 1 wherein said pulse forming network comprises means for selectively varying the interval of time between said treatment pulses.

6. The instrument of claim 1 wherein said determining means further determines said holding means impedance between successive ones or series of treatment pulses in order to change said matching means so that said holding means impedance matches said forming means impedance before the next successive treatment pulse is applied.

7. The instrument of claim 1 wherein said matching means comprises a plurality of resistors connected in parallel combination with said holding means and means operative with each of said resistors for selectively connecting each said resistor in parallel with said holding means until said impedance of said holding means matches said applying means.

8. The instrument of claim 7 wherein said matching means comprises:

means selectively connected across said parallel combination of said plurality of resistors and said holding means for delivering at least one signal to said combination, means connected to said delivering means for sensing the impedance of said combination, means connected to said sensing means for comparing the sensed impedance to said impedance of said applying means, said comparing means generating a value corresponding to the difference between said sensed impedance and said applying means impedance, means receptive of said value and connected to said connecting means for connecting a sufficient amount of said resistors in parallel with said holding means so that said holding means impedance matches said applying means impedance.

9. An instrument for electrically altering the membranes of vesicles in a suspension in order to perform vesicular alteration and electrostructuring of said membranes, said instrument comprising:

means for supplying voltage, means in said supplying means for varying the amplitude of said voltage, a pulse forming network selectively connected to said supplying means for forming one or a series of treatment pulses, means in said pulse forming network for varying the duration of said treatment pulses, a pair of electrodes, means receptive of said vesicles in said suspension for holding said suspension between said pair of electrodes, means connected to said pulse forming network for selectively delivering each of said pulses from said network across said electrodes in said holding means, a plurality of resistors connected in parallel across said electrodes for matching the impedance of said holding means containing said suspension to the impedance of said network, each of said resistors being selectively connectable in parallel, means connected to said resistors and selectively connecting to said electrodes in said holding means before the delivery of said treatment pulses from said delivering means for determining whether the impedance of said holding means containing said suspension matches the impedance of said network, said connecting means selectively connecting said resistors in parallel with said holding means until said holding means impedance matches said network impedance.

10. The instrument of claim 9 further comprising a plurality of separate pulse forming networks wherein each pulse forming network forms a different shaped treatment pulse.

11. The instrument of claim 10 wherein each of said pulse forming networks reside on a separate module which plugs into said instrument.

12. The instrument of claim 9 wherein said determining means further determines said holding means impedance between successive ones or series of said treatment pulses in order to change said matching means so that said holding means impedance matches said network impedance before the next series of treatment pulses are applied.

13. An instrument for electrically altering the membranes of vesicles in a suspension in order to perform vesicular alteration and electrostructuring of said membranes, said instrument comprising:

means for supplying voltage, means selectively connected to said supplying means for forming one or a series of treatment pulses, a pair of electrodes, means receptive of said vesicles in said suspension for holding said suspension between said pair of electrodes, means connected to said forming means for selectively delivering each of said treatment pulses from said forming means across said electrodes in said holding means, means connected in parallel across said electrodes for matching the impedance of said holding means containing said suspension to the impedance of said forming means, means connected to said matching means and selectively connecting to said electrodes in said holding means between successive treatment pulses from said delivering means for determining whether the impedance of said holding means matches the impedance of said forming means, said connecting means changing the impedance of said matching means until said holding means impedance matches said forming means impedance.

14. The instrument of claim 13 wherein said matching means comprises a plurality of resistors connected in parallel combination with said holding means and means operative with each of said resistors for selectively connecting each said resistor in parallel with said holding means until said impedance of said holding means matches said applying means.

15. The instrument of claim 14 wherein said matching means comprises:

means selectively connected across said parallel combination of said plurality of resistors and said holding means for delivering at least one signal to said combination, means connected to said delivering means for sensing the impedance of said combination, means connected to said sensing means for comparing the sensed impedance to said impedance of said applying means, said comparing means generating a value corresponding to the difference between said sensed impedance and said applying means impedance, means receptive of said value and connected to said connecting means for connecting a sufficient amount of said resistors in parallel with said holding means so that said holding means impedance matches said applying means impedance.

* * * * *